United States Patent
Watterson et al.

(10) Patent No.: US 7,537,546 B2
(45) Date of Patent: May 26, 2009

(54) SYSTEMS AND METHODS FOR CONTROLLING THE OPERATION OF ONE OR MORE EXERCISE DEVICES AND PROVIDING MOTIVATIONAL PROGRAMMING

(75) Inventors: Scott R. Watterson, Logan, UT (US); William T. Dalebout, North Logan, UT (US); Darren C. Ashby, Richmond, UT (US)

(73) Assignee: Icon IP, Inc., Logan, UT (US)

( * ) Notice: Subject to any disclaimer, the term of this patent is extended or adjusted under 35 U.S.C. 154(b) by 483 days.

(21) Appl. No.: 10/674,911

(22) Filed: Sep. 29, 2003

(65) Prior Publication Data

US 2004/0127335 A1 Jul. 1, 2004

Related U.S. Application Data

(63) Continuation-in-part of application No. 09/933,701, filed on Aug. 20, 2001, now Pat. No. 6,626,799, which is a continuation of application No. 09/349,608, filed on Jul. 8, 1999, now Pat. No. 6,312,363, application No. 10/674,911, filed on Sep. 29, 2003, which is a continuation-in-part of application No. 09/641,627, filed on Aug. 18, 2000, now Pat. No. 7,166,062, which is a continuation-in-part of application No. 09/349,608, filed on Jul. 8, 1999, now Pat. No. 6,312,363, and a continuation-in-part of application No. 09/496,560, filed on Feb. 2, 2000, now Pat. No. 6,447,424.

(51) Int. Cl.
*A63B 71/00* (2006.01)
(52) U.S. Cl. ............... 482/8; 482/1; 482/9; 482/54; 482/900
(58) Field of Classification Search ............ 482/1–9, 482/900–902, 51, 54; 434/247
See application file for complete search history.

(56) References Cited

U.S. PATENT DOCUMENTS 3,518,985 A 7/1970 Quinton ............ 128/2.06

(Continued)

FOREIGN PATENT DOCUMENTS

DE 41 00 559 A1 7/1991

(Continued)

OTHER PUBLICATIONS

DVD labeled "iFIT.com Media Coverage News Clips Ver. 3.0," dated Mar. 30, 2000.

(Continued)

*Primary Examiner*—Glenn Richman
(74) *Attorney, Agent, or Firm*—Workman Nydegger

(57) ABSTRACT

The present invention is directed to systems and methods for providing exercise devices with motivational programming. The programming includes motivational content and control signals, synchronized with the motivational content, for controlling operation of the exercise device. The motivational content includes audio and/or video designed to simulate a group exercise setting and optionally instructional and educational content for the benefit of a user. The control signals can be carried in wireless carrier signals and can include bytes of data that define changes to the value of one or more operating parameters of an exercise device. The control signals can control one or more operating parameters of one or more exercise devices, whether at once, or device specific.

43 Claims, 13 Drawing Sheets

U.S. PATENT DOCUMENTS

| | | | |
|---|---|---|---|
| 3,602,502 A | 8/1971 | Hampl | 272/69 |
| 3,903,613 A | 9/1975 | Bisberg | |
| 4,020,795 A | 5/1977 | Marks | |
| 4,112,928 A | 9/1978 | Putsch | 128/2.05 R |
| 4,151,988 A | 5/1979 | Nabinger | 262/69 |
| 4,220,996 A | 9/1980 | Searcy | |
| 4,358,105 A | 11/1982 | Sweeney, Jr. | 272/73 |
| 4,542,897 A | 9/1985 | Melton et al. | |
| 4,544,152 A | 10/1985 | Taitel | 272/69 |
| 4,549,044 A | 10/1985 | Durham | 179/5 R |
| 4,571,682 A | 2/1986 | Silverman et al. | 364/413 |
| 4,642,769 A | 2/1987 | Petrofsky | 364/415 |
| 4,659,074 A | 4/1987 | Taitel et al. | 272/69 |
| 4,687,195 A | 8/1987 | Potts | 272/69 |
| 4,702,475 A | 10/1987 | Elstein et al. | |
| 4,708,337 A | 11/1987 | Shyu | 272/69 |
| 4,708,837 A | 11/1987 | Baxter et al. | |
| 4,765,613 A | 8/1988 | Voris | |
| 4,818,234 A | 4/1989 | Redington et al. | |
| 4,828,257 A | 5/1989 | Dyer et al. | 272/129 |
| 4,842,266 A | 6/1989 | Sweeney, Sr. et al. | 272/69 |
| 4,842,274 A | 6/1989 | Oosthuizen et al. | 272/129 |
| 4,848,737 A | 7/1989 | Ehrenfield | 272/69 |
| 4,860,763 A | 8/1989 | Schminke | 128/707 |
| 4,889,108 A | 12/1989 | Bond et al. | |
| 4,927,136 A | 5/1990 | Leask | 272/69 |
| 4,934,694 A | 6/1990 | McIntosh | 272/129 |
| 4,938,474 A | 7/1990 | Sweeney et al. | |
| 4,949,993 A | 8/1990 | Stark et al. | |
| 4,959,713 A | 9/1990 | Morotomi et al. | 358/108 |
| 4,998,725 A | 3/1991 | Watterson et al. | 272/129 |
| 5,020,795 A | 6/1991 | Airy et al. | 272/129 |
| 5,054,774 A | 10/1991 | Belsito | 272/130 |
| 5,062,632 A | 11/1991 | Dalebout et al. | 272/129 |
| 5,067,710 A | 11/1991 | Watterson et al. | 272/129 |
| 5,078,152 A | 1/1992 | Bond et al. | 128/774 |
| 5,086,385 A | 2/1992 | Launey et al. | 364/188 |
| 5,104,120 A | 4/1992 | Watterson et al. | 482/5 |
| 5,113,427 A | 5/1992 | Ryoichi et al. | 379/57 |
| 5,137,501 A | 8/1992 | Mertesdorf | |
| 5,145,475 A | 9/1992 | Cares | 482/52 |
| 5,149,084 A | 9/1992 | Dalebout et al. | 482/3 |
| 5,195,935 A | 3/1993 | Fencel | 482/70 |
| 5,201,772 A | 4/1993 | Maxwell | |
| 5,213,555 A | 5/1993 | Hood et al. | 482/57 |
| 5,230,673 A | 7/1993 | Maeyama et al. | |
| 5,243,998 A | 9/1993 | Silverman et al. | |
| 5,254,066 A | 10/1993 | Brown et al. | |
| 5,256,115 A | 10/1993 | Scholder et al. | |
| 5,277,678 A | 1/1994 | Friedebach et al. | |
| 5,290,205 A | 3/1994 | Densmore et al. | |
| 5,292,293 A | 3/1994 | Schumacher | |
| 5,299,810 A * | 4/1994 | Pierce et al. | 463/2 |
| 5,308,296 A | 5/1994 | Eckstein | 482/5 |
| 5,308,300 A | 5/1994 | Chino et al. | |
| 5,313,942 A | 5/1994 | Platzker | 128/639 |
| 5,314,391 A | 5/1994 | Potash et al. | 482/7 |
| 5,318,487 A | 6/1994 | Golen et al. | |
| 5,318,491 A | 6/1994 | Houston | |
| D348,493 S | 7/1994 | Ashby | D21/192 |
| 5,328,420 A | 7/1994 | Allen | 482/52 |
| 5,328,422 A | 7/1994 | Nichols | 482/52 |
| 5,335,188 A | 8/1994 | Brisson | |
| 5,352,166 A | 10/1994 | Chang | 482/52 |
| 5,382,209 A | 1/1995 | Pasier et al. | 482/70 |
| 5,385,519 A | 1/1995 | Hsu et al. | |
| 5,385,520 A | 1/1995 | Lepine et al. | |
| 5,387,164 A | 2/1995 | Brown, Jr. | 482/9 |
| 5,403,252 A | 4/1995 | Leon et al. | |
| 5,407,402 A | 4/1995 | Brown et al. | |
| 5,410,471 A | 4/1995 | Alyfuku et al. | 364/413.02 |
| 5,410,472 A | 4/1995 | Anderson | 364/413.04 |
| 5,433,679 A | 7/1995 | Szymczak et al. | 482/54 |
| 5,435,799 A | 7/1995 | Lundin | |
| 5,451,922 A | 9/1995 | Hamilton | |
| 5,462,051 A | 10/1995 | Oka et al. | 128/630 |
| 5,462,504 A | 10/1995 | Trulaske et al. | 482/7 |
| 5,466,200 A | 11/1995 | Ulrich et al. | 482/4 |
| 5,474,090 A | 12/1995 | Begun et al. | 128/707 |
| 5,484,389 A | 1/1996 | Stark et al. | |
| 5,489,249 A | 2/1996 | Brewer et al. | 482/5 |
| 5,512,025 A | 4/1996 | Dalebout et al. | 482/6 |
| 5,527,239 A | 6/1996 | Abbondanza | 482/8 |
| 5,535,664 A | 7/1996 | Rokowski | 99/331 |
| 5,538,486 A | 7/1996 | France et al. | |
| 5,547,439 A * | 8/1996 | Rawls et al. | 482/5 |
| 5,584,779 A | 12/1996 | Knecht et al. | |
| 5,591,104 A | 1/1997 | Andrus et al. | 482/7 |
| 5,600,310 A | 2/1997 | Whipple, III et al. | 340/825 |
| 5,619,412 A | 4/1997 | Hapka | 364/424 |
| 5,619,991 A | 4/1997 | Sloane | 128/630 |
| 5,626,539 A | 5/1997 | Piaget et al. | 482/54 |
| 5,645,509 A | 7/1997 | Brewer et al. | 482/4 |
| 5,667,459 A | 9/1997 | Su | |
| 5,690,852 A | 11/1997 | Saito et al. | |
| 5,697,834 A | 12/1997 | Heumann et al. | 451/440 |
| 5,702,323 A | 12/1997 | Poulton | 482/8 |
| 5,704,875 A | 1/1998 | Tanabe | |
| 5,720,771 A | 2/1998 | Snell | 607/60 |
| 5,722,418 A | 3/1998 | Bro | 128/732 |
| 5,738,612 A | 4/1998 | Tsuda | 482/8 |
| 5,743,833 A | 4/1998 | Watterson et al. | 482/54 |
| 5,749,372 A | 5/1998 | Allen et al. | 482/8 |
| 5,752,897 A | 5/1998 | Skowronski et al. | 482/54 |
| 5,759,199 A | 6/1998 | Snell et al. | 607/60 |
| 5,777,678 A | 7/1998 | Ogata et al. | |
| 5,779,596 A | 7/1998 | Weber | 482/4 |
| 5,785,630 A | 7/1998 | Bobick et al. | |
| 5,785,631 A | 7/1998 | Heidecke | |
| 5,810,696 A | 9/1998 | Webb | 482/52 |
| 5,836,770 A * | 11/1998 | Powers | 434/247 |
| 5,845,230 A | 12/1998 | Lamberson | 702/56 |
| 5,857,939 A | 1/1999 | Kaufman | 482/8 |
| 5,865,733 A | 2/1999 | Malinouskas et al. | 600/300 |
| 5,873,369 A | 2/1999 | Lanaido et al. | 128/903 |
| 5,880,677 A | 3/1999 | Lestician | 340/825.06 |
| 5,888,172 A | 3/1999 | Andrus et al. | 482/7 |
| 5,890,906 A | 4/1999 | Macri et al. | |
| 5,890,995 A | 4/1999 | Bobick et al. | 482/4 |
| 5,905,442 A | 5/1999 | Mosebrook et al. | 340/825.06 |
| 5,911,132 A | 6/1999 | Sloane | 705/3 |
| 5,911,687 A | 6/1999 | Sato et al. | 600/300 |
| 5,916,063 A | 6/1999 | Alessandri | 482/4 |
| 5,917,405 A | 6/1999 | Joao | 340/426 |
| 5,929,748 A | 7/1999 | Odinak | 340/310.01 |
| 5,929,782 A | 7/1999 | Stark | 340/870.01 |
| 5,931,763 A | 8/1999 | Alessandri | 482/4 |
| 5,947,869 A | 9/1999 | Shea | |
| 5,961,561 A | 10/1999 | Wakefield, II | 701/29 |
| 5,964,701 A | 10/1999 | Asada et al. | 600/300 |
| 5,967,975 A | 10/1999 | Ridgeway | 600/300 |
| 5,993,356 A | 11/1999 | Houston et al. | |
| 5,995,868 A | 11/1999 | Dorfmeister et al. | 600/544 |
| 5,997,476 A | 12/1999 | Brown | 600/300 |
| 6,010,451 A | 1/2000 | Clawson | 600/300 |
| 6,013,007 A | 1/2000 | Root et al. | 482/8 |
| 6,014,432 A | 1/2000 | Modney | 379/106.02 |
| 6,033,344 A | 3/2000 | Trulaske et al. | 482/7 |
| 6,042,519 A | 3/2000 | Shea | 482/57 |
| 6,050,822 A | 4/2000 | Faughn | 434/11 |
| 6,050,924 A * | 4/2000 | Shea | 482/57 |
| 6,050,942 A | 4/2000 | Rust et al. | |
| 6,053,737 A | 4/2000 | Babbitt et al. | 434/30 |
| 6,053,844 A | 4/2000 | Clem | 482/8 |

| | | |
|---|---|---|
| 6,059,692 A | 5/2000 | Hickman ............. 482/8 |
| 6,066,705 A | 5/2000 | Calderon et al. |
| 6,106,297 A | 8/2000 | Pollak et al. ............ 434/16 |
| 6,132,337 A | 10/2000 | Krupka et al. ............ 482/8 |
| 6,148,262 A | 11/2000 | Fry |
| 6,152,854 A | 11/2000 | Carmein ............. 482/4 |
| 6,152,856 A | 11/2000 | Studor et al. ............ 482/8 |
| 6,162,151 A | 12/2000 | Tani et al. |
| 6,162,189 A | 12/2000 | Girone et al. |
| 6,171,186 B1 * | 1/2001 | Kurosawa et al. ............ 463/31 |
| 6,193,631 B1 | 2/2001 | Hickman ............. 482/8 |
| 6,211,451 B1 | 4/2001 | Tohgi et al. ............ 84/470 R |
| 6,231,481 B1 | 5/2001 | Brock ............. 482/8 |
| 6,231,482 B1 | 5/2001 | Thompson ............ 482/37 |
| 6,244,988 B1 | 6/2001 | Delman ............. 482/8 |
| 6,251,048 B1 | 6/2001 | Kaufman ............. 482/8 |
| 6,312,363 B1 | 11/2001 | Watterson et al. ............ 482/54 |
| 6,322,451 B1 * | 11/2001 | Miura ............. 463/42 |
| 6,356,856 B1 | 3/2002 | Damen et al. |
| 6,358,187 B1 | 3/2002 | Smith ............. 482/4 |
| 6,371,850 B1 * | 4/2002 | Sonoda ............. 463/8 |
| 6,450,922 B1 | 9/2002 | Henderson et al. |
| 6,458,060 B1 | 10/2002 | Watterson et al. ............ 482/54 |
| 6,463,385 B1 | 10/2002 | Fry |
| 6,464,618 B1 | 10/2002 | Shea ............. 428/8 |
| 6,475,115 B1 | 11/2002 | Candito et al. ............. 482/4 |
| 6,497,638 B1 | 12/2002 | Shea ............. 482/8 |
| 6,503,173 B2 | 1/2003 | Clem |
| 6,582,342 B2 | 6/2003 | Kaufman ............. 482/8 |
| 6,585,622 B1 * | 7/2003 | Shum et al. ............. 482/8 |
| 6,601,016 B1 | 7/2003 | Brown et al. ............. 702/8 |
| 6,605,020 B1 | 8/2003 | Huang |
| 6,605,038 B1 | 8/2003 | Teller et al. |
| 6,626,799 B2 | 9/2003 | Watterson et al. |
| 6,634,992 B1 | 10/2003 | Ogawa ............. 482/8 |
| 6,638,198 B1 | 10/2003 | Shea ............. 482/8 |
| 6,648,798 B2 | 11/2003 | Yoo |
| 6,659,946 B1 | 12/2003 | Batchelor et al. |
| 6,687,535 B2 | 2/2004 | Hautala et al. |
| 6,689,057 B1 | 2/2004 | Shinsel et al. |
| 6,702,719 B1 | 3/2004 | Brown et al. |
| 6,736,759 B1 | 5/2004 | Stubbs et al. |
| 6,740,007 B2 | 5/2004 | Gordon et al. |
| 6,749,537 B1 | 6/2004 | Hickman |
| 6,783,482 B2 | 8/2004 | Oglesby et al. |
| 6,786,848 B2 | 9/2004 | Yamashita et al. |
| 6,790,178 B1 | 9/2004 | Mault et al. |
| 6,793,607 B2 | 9/2004 | Neil |
| 6,808,472 B1 | 10/2004 | Hickman |
| 6,808,473 B2 | 10/2004 | Hisano et al. |
| 6,824,502 B1 | 11/2004 | Huang |
| 6,825,876 B1 | 11/2004 | Easwar et al. |
| 6,863,641 B1 | 3/2005 | Brown et al. |
| 6,866,613 B1 | 3/2005 | Brown et al. |
| 6,918,858 B2 | 7/2005 | Watterson et al. |
| 6,921,351 B1 | 7/2005 | Hickman et al. |
| 6,991,586 B2 | 1/2006 | Lapcevic |
| 6,997,852 B2 | 2/2006 | Watterson et al. |
| 7,022,047 B2 | 4/2006 | Cohen et al. |
| 7,044,891 B1 | 5/2006 | Rivera |
| 7,056,265 B1 | 6/2006 | Shea |
| 7,060,006 B1 | 6/2006 | Watterson et al. |
| 7,060,008 B2 | 6/2006 | Watterson et al. |
| 7,070,539 B2 | 7/2006 | Brown et al. |
| 7,072,789 B2 | 7/2006 | Vock et al. |
| 7,115,076 B2 | 10/2006 | Oglesby et al. |
| 7,128,693 B2 | 10/2006 | Brown et al. |
| 7,166,062 B1 | 1/2007 | Watterson et al. |
| 7,166,064 B2 | 1/2007 | Watterson et al. |
| 7,254,516 B2 | 8/2007 | Case, Jr. et al. |
| 7,350,787 B2 | 4/2008 | Voss |
| 7,354,380 B2 | 4/2008 | Volpe, Jr. |
| 2004/0162189 A1 | 8/2004 | Hickman |
| 2005/0233859 A1 | 10/2005 | Takai et al. |
| 2005/0233861 A1 | 10/2005 | Hickman et al. |
| 2005/0261609 A1 | 11/2005 | Collings et al. |
| 2006/0205566 A1 | 9/2006 | Watterson et al. |
| 2006/0205569 A1 | 9/2006 | Watterson et al. |
| 2006/0281603 A1 | 12/2006 | Hickman |
| 2007/0265138 A1 | 11/2007 | Ashby |
| 2008/0051256 A1 | 2/2008 | Ashby et al. |

FOREIGN PATENT DOCUMENTS

| | | |
|---|---|---|
| EP | 0 199 442 | 10/1986 |
| JP | H10-243979 | 9/1998 |
| WO | WO 98/32496 | 7/1998 |

OTHER PUBLICATIONS

*Exergaming,* en.wikipedia.org, printed Oct. 1, 2007 (4 pages).
*Wired,* www.wired.com, issue 2.09, Sep. 1994 (4 pages).
"Defendant's Amended Invalidity Contentions," Case No. 2:05-cv-527, signed by Kirk Harris on Mar. 16, 2007 (15 pages).
"Icon Health & Fitness, Inc.'s Supplemental Preliminary Invalidity Contentions," Case No. 2:05-cv-527, signed by Brent A. Hansen on Jun. 23, 2006 (24 pages).
"Icon Health & Fitness, Inc.'s Preliminary Invalidity Contentions," Case No. 2:05-cv-527, signed by Brett A. Hansen on Jun. 26, 2006 (378 pages).
"Expert Report of Dr. Brent Nelson Pursuant to Federal Rule of Civil Procedure 26(a)(2)(B)," dated Mar. 13, 2007 (372 pages).
"Netpulse Brings Free Internet Access to Fitness Centers." Newsbytes.com, http://www.newsbytes.com, Jan. 17, 2000 (1 page).
"Precor and Netpulse Partner to Create the World's First Internet Powered Elliptical." Netpulse press release, Oct. 1, 1999 (2 pages).
"Surf While You Sweat." ABCNEWS.com, Oct. 27, 1998 (3 pages).
"The Best Products of 1999—Business Week's Top Picks of the Most Innovative Products on the Market." Business Week, Dec. 6, 1999 (2 pages).
Netpulse brochure. "Catch the wwwave," available on information and belief at least as early as Feb. 10, 2000 (6 pages).
Winkler, William J., "Pumping Iron With a Digital Friend," Business Week, Dec. 18, 1995, pp. 78a.
Internet Archive Wayback Machine, archive for www.ifit.com, at http://web.archive,org/web/*/www.ifit.com, Sep. 1, 2003, 1pg.
iFIT.com "Internet Workouts Control Your Treadmill, Bike, or Elliptical," at http://www.ifit.com, Sep. 1, 2003, 3 pages.
Icon Health and Fitness, Nordictrack C2420 (Model No. NTL14950), 2004.
Icon Health and Fitness, Nordictrack C2420 (Model No. NTL14951), 2004.
Icon Health and Fitness, Nordictrack C2420 (Model No. NTL1495.2), 2004.
Icon Health and Fitness, Nordictrack CX 990 (Model No. NEL09940), 2003.
Icon Health and Fitness, Nordictrack SL 760 (Model No. NTC89021), 2004.
Icon Health and Fitness, Nordictrack SL 760 (Model No. NTC89020), 2004.
Icon Health and Fitness, Nordictrack SL 710 (Model No. NTC07942), 2004.
Icon Health and Fitness, Nordictrack SL 710 (Model No. NTC07941), 2004.
Icon Health and Fitness, Nordictrack SL 710 (Model No. NTC07940), 2003.
Icon Health and Fitness, Nordictrack SL 705 (Model No. NTC05941), 2004.
Icon Health and Fitness, Nordictrack SL 705 (Model No. NTC05940), 2004.
Icon Health and Fitness, Nordictrack C2420 Manual preceding Specs, 2004.
Icon Health and Fitness, Pro-Form Personal Trainer Plus, undated.
Icon Health and Fitness, Screenshots of iFit.com, undated.
Icon Health and Fitness, iFit.com "Log on. Work out." Brochure, 2000.
Icon Health and Fitness, Website printouts (archived docs), 2000.

Icon Health and Fitness, Pro-Form 600 (Model No. PETL60000), 2000.
Icon Health and Fitness Inc., Reebok ACD1 (Model No. RETL11900), 2000.
Icon Health and Fitness Inc., Reebok RT1000 (Model No. RETL16001), 2001.
Icon Health and Fitness Inc., One-on-One Video Trainer (Model No. TLTL21040), 1995.
IEEE Computer Graphics and Applications—EVAC: A Virtual Environment for Control of Remote Imaging Instrumentation, 1996.
IEEE: Performance Analysis of a Gateway Connecting the Cebus to the ISDN, 1993.
Fitness Equipment: Cardio, 1997.
Icon Health and Fitness Inc., Photographs of various fitness equipment systems, 1989-1996.
Mademoiselle, www.IFIT.Com, Mademoiselle, Mar. 2000.
Wired, Icon Health & Fitness Image 10.4Qi, Wired, Apr. 2000.
Cooking Light, Cybertrainers are Watching Your Workout, Cooking Light, Aug. 2000.
Villarosa, A Fitness Industry, With Gadgets Galore, the New York Times, Apr. 25, 2000.
Little, Web Creates Workouts With Virtual Trainers, The Birmingham News, Apr. 10, 2000.
San Francisco Chronicle, Let the Web Help You Get Physical, Mar. 16, 2000.
DVD Labeled "Icon-CYB001" 881 PDF Files Jun. 12, 2006
CD-Rom Labeled "Supershow 2000," Icon-CYB 034309 Highlight Video Apr. 20, 2006.
CD-Rom Labeled "Supershow 1998," Icon-CYB 034310 Live Video Streaming from Logan, Utah to Atlanta, Georgia, Feb. 10, 1998.
DVD Lableled "1998 Supershow Web Cast," Icon-CYB 034311 Raw video footage, Jun. 2006.
CD-Rom Labeled "Steve Young Webcast," Icon-CYB 034312, Sales Meeting 2000, Jun. 2006.
Final Office Action dated May 6, 2008 for U.S. Appl. No. 10/856,676, filed May 28, 2004.
Non-final Office Action dated May 1, 2008 for U.S. Appl. No. 11/849,068, filed Aug. 31, 2007.
Restriction Requirement Action dated Apr. 28, 2008 for U.S. Appl. No. 11/150,914, filed Jun. 13, 2005.
Office Action dated Sep. 11, 2000, 3 pages, U.S. Appl. No. 09/349,608.
Notice of Allowance and Issue Fee Due, date mailed Jul. 25, 2001, 2 pages, U.S. Appl. No.09/349,608.
Notice of Allowance and Fee(s) Due, date mailed Sep. 20, 2004, 7 pages, U.S. Appl. No. 09/641,627.
Restriction Requirement dated Apr. 29, 2005, 4 pages, U.S. Appl. No. 09/641,627.
Office Action dated Jul. 26, 2005, 4 pages, U.S. Appl. No. 09/641,627.
Notice of Allowance and Fee(s) Due, date mailed Feb. 3, 2006, 4 pages, U.S. Appl. No. 09/641,627.
Notice of Allowance and Fee(s) Due, date mailed Sep. 1, 2006, 4 pages, U.S. Appl. No. 09/641,627.
Restriction Requirement dated Apr. 17, 2007, 5 pages, U.S. Appl. No. 11/429,858.
Office Action dated Aug. 22, 2007, 5 pages, U.S. Appl. No. 11/429,858.
Restriction Requirement dated Feb. 5, 2008, 8 pages, U.S. Appl. No. 11/429,858.
Restriction Requirement dated Sep. 23, 2003, 4 pages, U.S. Appl. No. 09/641,600.
Office Action dated Feb. 11, 2004, 4 pages, U.S. Appl. No. 09/641,600.
Notice of Allowance and Fee(s) Due, date mailed Jun. 2, 2004, 4 pages, U.S. Appl. No. 09/641,600.
Office Action dated Feb. 15, 2005, 7 pages, U.S. Appl. No. 09/641,600.
Notice of Allowance and Fee(s) Due, date mailed Sep. 14, 2005, 4 pages, U.S. Appl. No. 09/641,600.
Office Action dated Dec. 18, 2001, 3 pages, U.S. Appl. No. 09/641,220.
Notice of Allowance and Fee(s) Due, date mailed Jul. 1, 2002, 5 pages, U.S. Appl. No. 09/641,220.
Office Action dated Jun. 29, 2004, 3 pages, U.S. Appl. No. 09/776,410.
Notice of Allowance and Fee(s) Due, date mailed Nov. 12, 2004, 4 pages, U.S. Appl. No. 09/776,410.
Notice of Allowance and Fee(s) Due, date mailed Apr. 18, 2005, 5 pages, U.S. Appl. No. 09/776,410.
Restriction Requirement dated Oct. 9, 2007, 5 pages, U.S. Appl. No. 10/856,676.
Office Action dated Jan. 24, 2008, 5 pages, U.S. Appl. No. 10/856,676.
Restriction Requirement dated Jul. 1, 2003, 4 pages, U.S. Appl. No. 09/947,193.
Office Action dated Oct. 23, 2003, 4 pages, U.S. Appl. No. 09/947,193.
Notice of Allowance and Fee(s) Due, date mailed May 14, 2004, 4 pages, U.S. Appl. No. 09/947,193.
Office Action dated Sep. 15, 2005, 5 pages, U.S. Appl. No. 09/947,193.
Notice of Allowance and Fee(s) Due, date mailed Jan. 26, 2006, 5 pages, U.S. Appl. No. 09/947,193.
Notice of Allowance and Fee(s) Due, date mailed Aug. 16, 2006, 4 pages, U.S. Appl. No. 09/947,193.
Restriction Requirement dated Mar. 26, 2007, 5 pages, U.S. Appl. No. 11/429,725.
Office Action dated Jun. 6, 2007, 5 pages, U.S. Appl. No. 11/429,725.
Restriction Requirement dated Nov. 14, 2007, 5 pages, U.S. Appl. No. 11/429,725.
Final Office Action dated Feb. 28, 2008, 8 pages, U.S. Appl. No. 11/429,725.
Restriction Requirement dated Sep. 21, 2004, 4 pages, U.S. Appl. No. 10/106,842.
Office Action dated Nov. 12, 2004, 4 pages, U.S. Appl. No. 10/106,842.
Notice of Allowance and Fee(s) Due, date mailed Mar. 14, 2005, 6 pages, U.S. Appl. No. 10/106,842.
Notice of Allowance and Fee(s) Due, date mailed Mar. 29, 2006, 6 pages, U.S. Appl. No. 11/132,740.
Notice of Allowance and Fee(s) Due, date mailed Jun. 30, 2003, 5 pages, U.S. Appl. No. 09/933,701.
Office Action dated Jun. 16, 1997, 4 pages, U.S. Appl. No. 08/766,513.
Office Action dated Feb. 17, 1998, 5 pages, U.S. Appl. No. 08/766,513.
Notice of Allowance and Issue Fee Due, date mailed Sep. 22, 1998, 3 pages, U.S. Appl. No. 08/766,513.
Response to Rule 312 Communication, dated Jun. 2, 1999, 2 pages, U.S. Appl. No. 08/766,513.
Office Action dated Dec. 10, 1999, 3 pages, U.S. Appl. No. 09/273,591.
Notice of Allowance and Fee(s) Due, date mailed Jul. 14, 2000, 2 pages, U.S. Appl. No. 09/273,591.
Office Action dated Dec. 18, 2001, 3 pages, U.S. Appl. No. 09/690,701.
Office Action dated Sep. 25, 2002, 4 pages, U.S. Appl. No. 09/690,701.
Final Office Action dated Mar. 21, 2003, 4 pages, U.S. Appl. No. 09/690,701.
Advisory Action dated Jun. 16, 2003, 2 pages, U.S. Appl. No. 09/690,701.
Notice of Allowance and Fee(s) Due, date mailed Nov. 24, 2003, 5 pages, U.S. Appl. No. 09/690,701.
Restriction Requirement dated Dec. 29, 2004, 4 pages, U.S. Appl. No. 10/729,356.
Office Action dated Feb. 16, 2005, 5 pages, U.S. Appl. No. 10/729,356.
Restriction Requirement dated Feb. 21, 2006, 5 pages, U.S. Appl. No. 10/729,356.
Notice of Allowance and Fee(s) Due, date mailed Jun. 13, 2006, 6 pages, U.S. Appl. No. 10/729,356.
Response to Rule 312 Communication, dated Jul. 30, 2007, 2 pages, U.S. Appl. No. 10/729,356.

Office Action dated Jan. 14, 2008, 7 pages, U.S. Appl. No. 10/729,356.
Office Action dated Jan. 24, 2005, 4 pages, U.S. Appl. No. 10/773,617.
Notice of Allowance and Fee(s) Due, date mailed Apr. 17, 2006, 4 pages, U.S. Appl. No. 10/773,617.
Notice of Allowance and Fee(s) Due, date mailed Jul. 6, 2006, 4 pages, U.S. Appl. No. 10/773,617.
Office Action dated May 16, 2007, 4 pages, U.S. Appl. No. 10/773,617.
Office Action dated Jan. 24, 2008, 8 pages, U.S. Appl. No. 10/773,617.
Final Office Action dated Apr. 24, 2008, 10 pages, U.S. Appl. No. 10/773,617.
Office Action dated Dec. 18, 2001, 3 pages, U.S. Appl. No. 09/690,178.
Notice of Allowance and Fee(s) Due, date mailed Sep. 23, 2002, 5 pages, U.S. Appl. No. 09/690,178.
Office Action dated Mar. 7, 2003, 4 pages, U.S. Appl. No. 09/690,178.
Notice of Allowance and Fee(s) Due, date mailed Nov. 24, 2003, 4 pages, U.S. Appl. No. 09/690,178.
Response to Rule 312 Communication, dated Jan. 21, 2004, 2 pages, U.S. Appl. No. 09/690,178.
Office Action dated Jan. 27, 2005, 6 pages, U.S. Appl. No. 10/751,334.
Final Office Action dated Aug. 25, 2005, 6 pages, U.S. Appl. No. 10/751,334.
Notice of Allowance and Fee(s) Due, date mailed Jun. 12, 2006, 4 pages, U.S. Appl. No. 10/751,334.
Restriction Requirement dated Apr. 17, 2007, 5 pages, U.S. Appl. No. 10/751,334.
Restriction Requirement dated Aug. 9, 2007, 5 pages, U.S. Appl. No. 10/751,334.
Office Action dated Jan. 25, 2008, 7 pages, U.S. Appl. No. 10/751,334.
Office Action dated Jun. 15, 2004, 4 pages, U.S. Appl. No. 10/045,619.
Notice of Allowance and Fee(s) Due, date mailed Mar. 14, 2005, 4 pages, U.S. Appl. No. 10/045,619.
Restriction Requirement dated Jul. 27, 2006, 5 pages, U.S. Appl. No. 11/150,914.
Restriction Requirement dated Oct. 18, 2006, 5 pages, U.S. Appl. No. 11/150,914.
Office Action dated Feb. 22, 2007, 6 pages, U.S. Appl. No. 11/150,914.
Final Office Action dated Dec. 12, 2007, 8 pages, U.S. Appl. No. 11/150,914.
Advisory Action dated Feb. 7, 2008, 3 pages, U.S. Appl. No. 11/150,914.
*Consumer Reports, Out of the Rat Race, onto a Treadmill*, Feb. 2000 (5 pages).
*Consumer Reports, Out of the Rat Race, onto a Treadmill* at http://www.accessmylibrary.com/coms2/summaryU0286-28004514_ITM, Mar. 5, 2007, 8 pages.

Notice of Allowance and Fee(s) Due, date mailed Jun. 4, 2008, 8 pages, U.S. Appl. No. 11/429,858.
Notice of Allowance and Fee(s) Due, date mailed Jun. 4, 2008, 9 pages, U.S. Appl. No. 11/429,725.
Final Office Action dated Jun. 2, 2008, 7 pages, U.S. Appl. No. 10/751,334.
Non-final Office Action dated Jun. 13, 2008, 6 pages, U.S. Appl. No. 11/657,701.
Non-final Office Action dated Jun. 26, 2008, 4 pages, U.S. Appl. No. 11/440,703.
Final Office Action dated Jul. 1, 2008, 9 pages, U.S. Appl. No. 10/729,356.
Office Action dated Aug. 21, 2008, 6 pages, U.S. Appl. No. 11/849,068.
Notice of Allowance and Fee(s) Due dated Aug. 8, 2008, 4 pages, U.S. Appl. No. 11/429,858.
Notice of Allowance and Fee(s) Due dated Sep. 8, 2008, 4 pages, U.S. Appl. No. 11/429,725.
Notice of Allowance and Fee(s) Due and Interview Summary dated Oct. 2, 2008, 8 pages, U.S. Appl. No. 10/856,676.
Office Action Summary dated Nov. 25, 2008, 6 pages, U.S. Appl. No. 10/751,334.
Office Action Summary dated Oct. 16, 2008, 9 pages, U.S. Appl. No. 10/773,617.
Office Action Summary dated Jun. 27, 2008, 13 pages, U.S. Appl. No. 11/833,070.
Office Action Summary dated Oct. 31, 2008, 23 pages, U.S. Appl. No. 11/833,070.
*The FitLinxx Interactive Fitness Network* TM, Integrated Fitness Corp., brochure, 1998 (4 pages).
Fitlinxx Interactive Fitness Network TM, *The Difference Between Surviving and Thriving May be as Simple as FitLinxx* TM, Integrated Fitness Corp., brochure, 1998 (1 page).
Forbes Digital Tool: Startups, *Sweat Equity,* www.forbes.com, Feb. 1998 (2 pages).
Netpulse, Networkingout—Coming Distractions: *Netpulse Helps Exercisers Surf the Net at the Gym, Accomplish Several Goals at Once,* www.netpulse.com, Apr. 1998 (3 pages).
Netpulse, *Instead of having an equipment repair technician traveling over hill and dale, you may soon have equipment repaired via the Internet,* www.netpulse.com, Jul. 1998 (3 pages).
Netpulse, *Infotech is supposed to make life easier-remember? Here's how to be sure it does.,* www.netpulse.com, Aug. 1998 (4 pages).
Netpulse, Exercise station connects to the Net, *Now you can sweat to the Net.,* www.netpulse.com, Sep. 1998 (1 page).
Netpulse, New Fitness Equipment Combines Internet, Sweat, *Now you can surf and sweat,* www.netpulse.com, Jan. 1999 (2 pages).
Netpulse, Hop In, Log On and Sweat, *Netpulse exercise machines are the latest Web feat,* www.netpulse.com, Feb. 1999 (2 pages).
Netpulse Club Watch TM, *Internet Powered Service,* brochure, Apr. 1999 (1 page).
Netpulse, *State of the Art,* www.netpulse.com, Feb. 2000 (1 page).
Netpulse, *Netpulse Files for Patents on its Pioneering Technology Inventions and Groundbreaking Business Methods in the Media and Fitness Markets,* www.netpulse.com, May 2000 (2 pages).

* cited by examiner

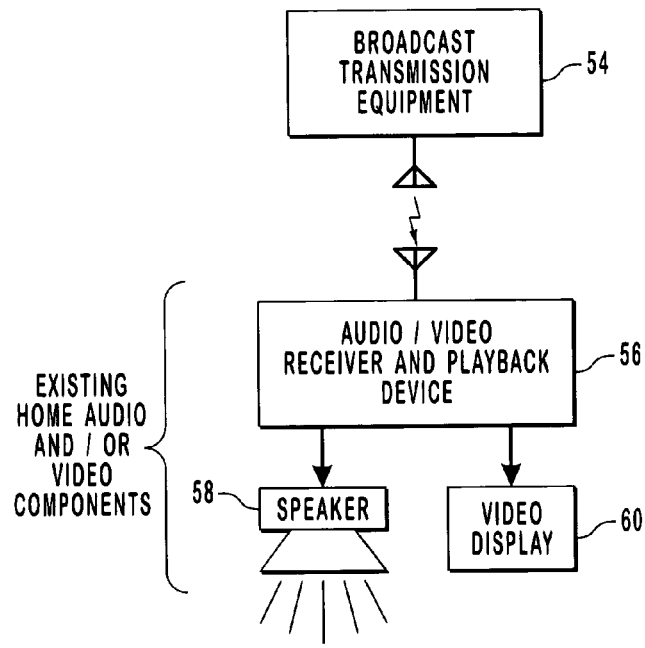
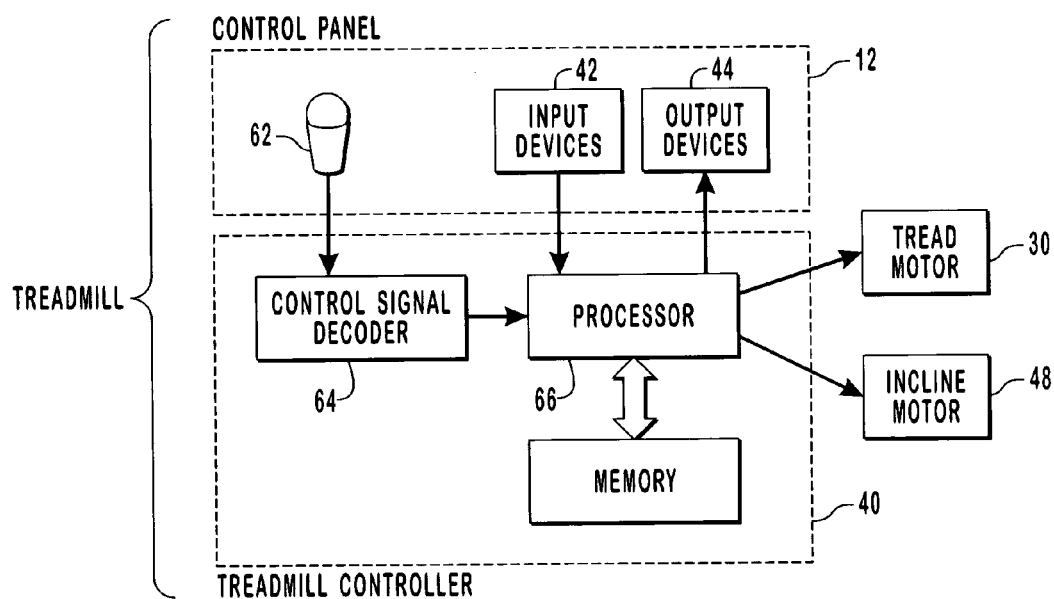
FIG. 5

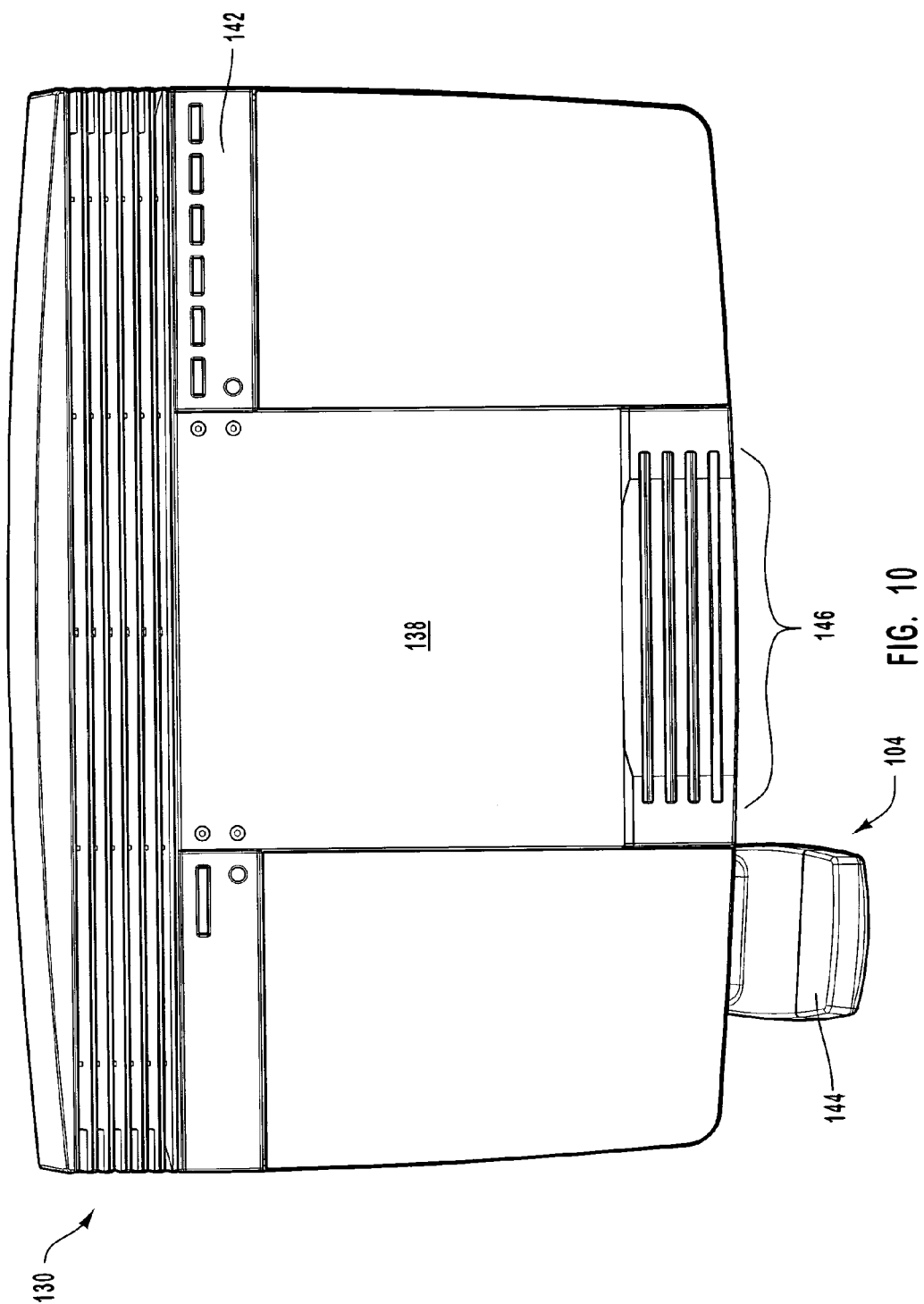

SYSTEMS AND METHODS FOR CONTROLLING THE OPERATION OF ONE OR MORE EXERCISE DEVICES AND PROVIDING MOTIVATIONAL PROGRAMMING

RELATED APPLICATIONS

This is a continuation-in-part application of (i) U.S. patent application Ser. No. 09/933,701, entitled "System And Methods For Providing An Improved Exercise Device With Motivational Programming," filed Aug. 20, 2001, which is a continuation application of U.S. patent application Ser. No. 09/349,608, filed Jul. 8, 1999 entitled "Systems and Methods for Providing an Improved Exercise Device with Motivational Programming", now U.S. Pat. No. 6,312,363; and (ii) a continuation-in-part application of U.S. patent application Ser. No. 09/641,627, filed Aug. 18, 2000 entitled "System for Interaction with Exercise Device", which is a continuation-in-part application of (A) patent application Ser. No. 09/349,608, filed Jul. 8, 1999 entitled "Systems and Methods for Providing an Improved Exercise Device with Motivational Programming", now U.S. Pat. No. 6,312,363, and (B) copending U.S. patent application Ser. No. 09/496,560, filed Feb. 2, 2000 entitled "System and Method for Selective Adjustment of Exercise Apparatus." Each of the aforementioned applications and patents is hereby incorporated herein in its entirety by reference.

BACKGROUND OF THE INVENTION

1. The Field of the Invention

This invention generally relates to exercise equipment and, more specifically, to systems and methods for controlling the operation of one or more exercise devices and providing motivational programming.

2. The Relevant Technology

In an attempt to improve their health and physical conditioning, consumers are purchasing home exercise devices or equipment in record quantities. One common problem with home exercise equipment is motivating the purchaser to use the device on a consistent and ongoing basis. In addition, many exercise devices involve repetitive actions, which can quickly become tedious and boring to a person exercising alone.

In recent years, health clubs have organized various exercise classes and routines involving a group setting. In the proper setting, a group approach to exercise creates a synergy, whereby individual members of the class derive encouragement and motivation from other members of the group. In addition, group settings promote a healthy sense of competition among group members. Initially, such group fitness and exercise classes typically involved aerobics, traditionally performed without the use of any ancillary exercise equipment or devices. In recent years, however, the group work out approach has been extended to classes that utilize various exercise devices. Take, for example, the recent rise in popularity of "Spinning Classes," in which each participant operates his or her own stationery exercise cycle in a group setting, with a coach or instructor leading the group through a prescribed program or routine. Similarly, with recent advances in the design of treadmills, it is possible to have "Treadmill Classes" wherein an instructor not only leads and motivates the group, but the instructor is also able to control the operation of the treadmills of all of the class participants from a single control panel.

One of the primary disadvantages with group training, however, is that it is typically available only at health clubs and, therefore, is not as convenient as exercising in the privacy and comfort of one's own home. It would be, therefore, an advancement in the art of home exercise equipment to provide the desirable benefits of group exercise by providing motivational exercise programming that simulates a group exercise setting in the home.

BRIEF SUMMARY OF THE INVENTION

The present invention is directed to systems and methods for providing exercise devices with motivational programming. The present invention is particularly well suited to exercise devices, whether aerobic or anaerobic exercise devices, which use one or more motors and/or other electrically driven actuators that control one or more operating parameters of the exercise device. Other embodiments of the present invention are well suited to exercise devices that do not include one or more motors and/or other electrically driven actuators, and can include wireless transmission and reception devices or systems.

The present invention contemplates the use of programming that includes motivational content and one or more control signals, synchronized with the motivational content, for controlling the operation of the exercise device. In one embodiment, the control signals can be distributed to an exercise device through a wireless transmission, such as an infrared (IR) or radio frequency (RF) transmission. These control signals change one or more operating parameters of the exercise device in accordance or synchronized with the motivational content. By so doing, the motivational content encourages the exercising user as embedded control signals vary the operating parameters of the exercise device as encouragement is provided to the user.

The motivational content forming part of the exercise programming can include audio and/or video designed to simulate a group exercise setting. In addition, the motivational content can include instructional and educational content for the benefit of the user. The programming, including motivational content and/or control signals, can be live or prerecorded and can be broadcast over conventional broadcast channels, cable, satellite, the internet, through RF, IR, or other wireless technologies, or any other means suitable for transmitting audio and/or video signals. Alternatively, the programming can be prerecorded and stored on a storage medium, such as audio cassette tapes, compact discs, minidiscs, videotapes, laser discs, digital video discs, computer diskettes, hard drive, or any other storage medium suitable for the storage and reproduction of audio and/or video signals.

The present invention also includes means for reproducing the programming, including the motivational content along with the synchronized control signals. The present invention includes means for transmitting, receiving, and decoding the control signals and for controlling the operation of the exercise device in synchronization with the motivational content.

Accordingly, the invention provides exercise devices that incorporate a standardized interface for receiving and decoding control signals embedded in multimedia programming for controlling various operating parameters of the exercise device in synchronization with the multimedia programming. By so doing, the present invention provides home exercise devices that are capable of simulating a group or class workout environment and synchronizing operation of the exercises devices with motivational programming.

The present invention also provides improved exercise devices, wherein programming containing motivational content and control signals can be reproduced using audio and/or video playback devices commonly found in the home, such as televisions, VCRs, home stereo equipment, and the like, and the exercise device can decode and utilize the control signals to synchronize operation of the exercise device with the motivational content.

The present invention also provides exercise devices that are responsive to control signals encoded in programming external to the exercise device and containing audio and/or video and that can be transmitted and received using conventional broadcasting technologies and wireless broadcast technologies.

The present invention also provides enhanced exercise devices, the operation of which can be controlled using interchangeable, multimedia programming containing motivational content and control signals that are synchronized with the motivational content.

Additionally, the invention provides an improved exercise machine that facilitates live, interactive communications between the exercise device user at home and a trainer or coach in a remote location, and which allows the trainer or coach to control the operating parameters of the user's exercise device on a live, real time basis.

Furthermore, the invention provides a central control unit that can provide wireless communications to one or more exercise devices, the central control unit dictating exercise parameters for the one or more exercise devices.

These advantages in addition to other objects and advantages of the invention will be set forth in the description which follows, and in part will be obvious from the description, or may be learned by the practice of the invention. The objects and advantages of the invention may be realized and obtained by means of the instruments and combinations particularly pointed out in the appended claims.

BRIEF DESCRIPTION OF THE DRAWINGS

In order that the manner in which the above-recited and other advantages and objects of the invention are obtained, a more particular description of the invention briefly described above will be rendered by reference to specific embodiments thereof that are illustrated in the appended drawings. Understanding that these drawings depict only typical embodiments of the invention and are not therefore to be considered to be limiting of its scope, the invention will be described and explained with additional specificity and detail through the use of the accompanying drawings in which:

FIG. 5 is a functional block diagram of one embodiment of the present invention;

FIG. 10 is a functional block diagram in accordance with an alternative embodiment of the present invention;

DETAILED DESCRIPTION OF THE PREFERRED EMBODIMENTS

The present invention is directed to exercise devices that include one or more motors or other electrically driven actuators used to control one or more operating parameters of the exercise device. The present invention includes a central control unit that can be used to control one or more exercise devices at once, whether controlled through physical or wireless connection. While the invention will be described in the context of a motorized treadmill, it should be understood that the invention is not limited to any particular type of exercise device, whether aerobic or anaerobic. To the contrary, the present invention can be readily adapted to any motorized exercise device or any other exercise device that utilizes stepper motors, solenoids, or any other electrically driven actuator to control any operating parameter of the device, such as speed, resistance, inclination, or other operating parameters.

As used herein, the term "exercise device" shall refer broadly to any type of aerobic or anaerobic exercise machine, including, but not limited to, treadmills, exercise cycles, nordic style ski exercise devices, rowers, steppers, elliptical or striding exercise devices, weight devices, resistance devices, and so forth.

Figure 1:
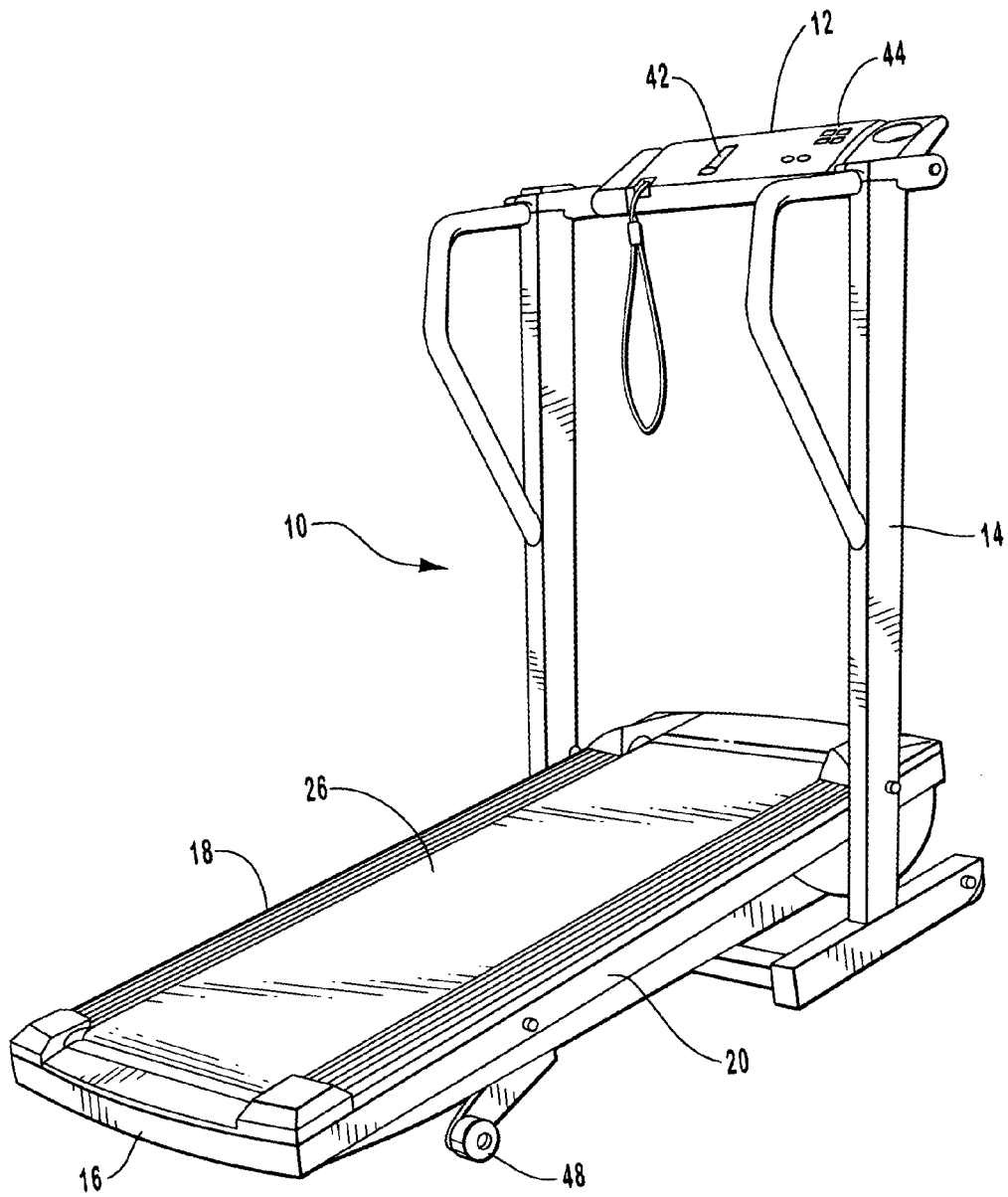
FIG. 1 is a perspective illustration of a reorienting treadmill with the tread base positioned in a first position for a user to perform exercises.
Figure 2:
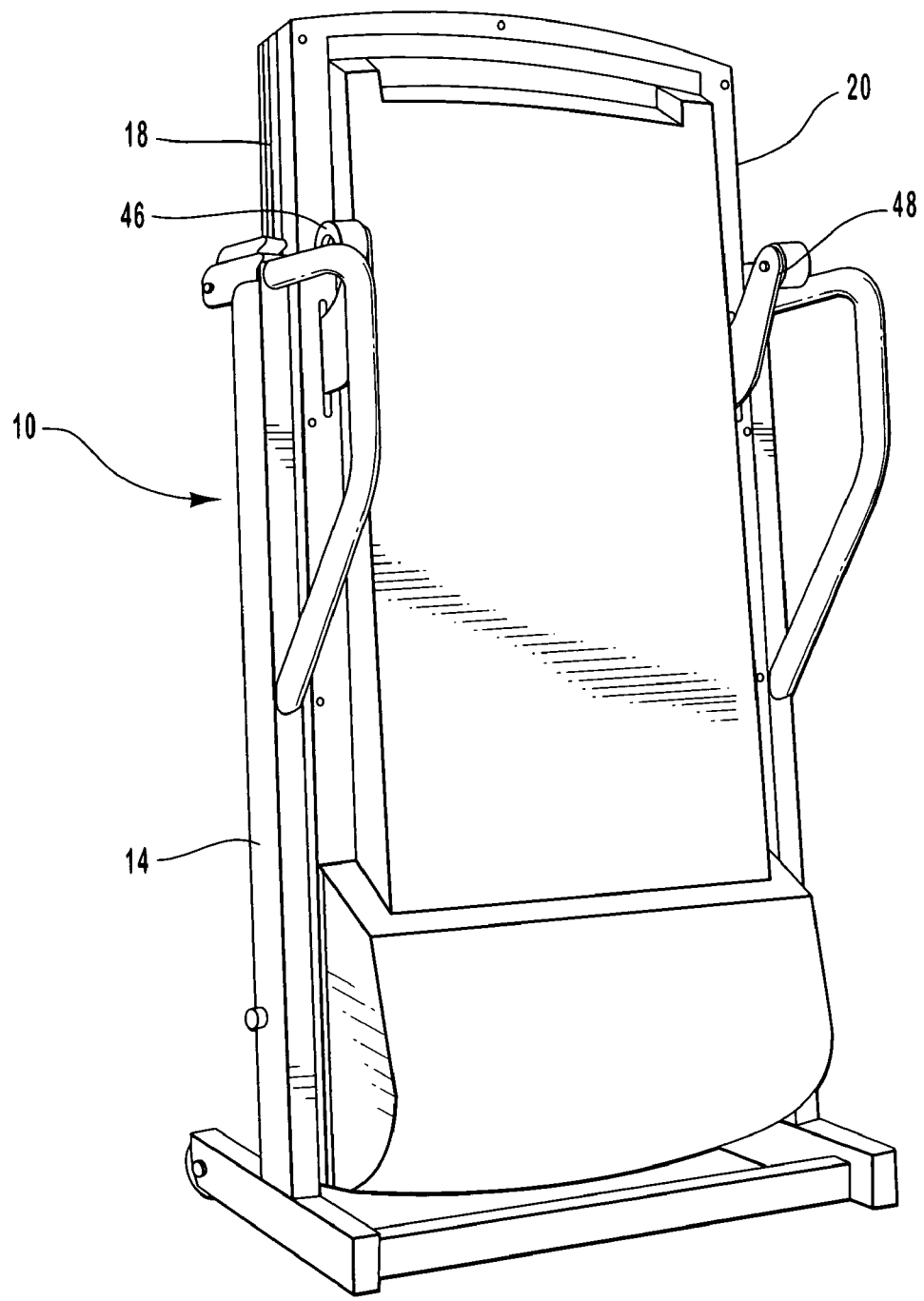
FIG. 2 is a perspective illustration of a reorienting treadmill with the tread base positioned in a second or storage position.
Figure 3:
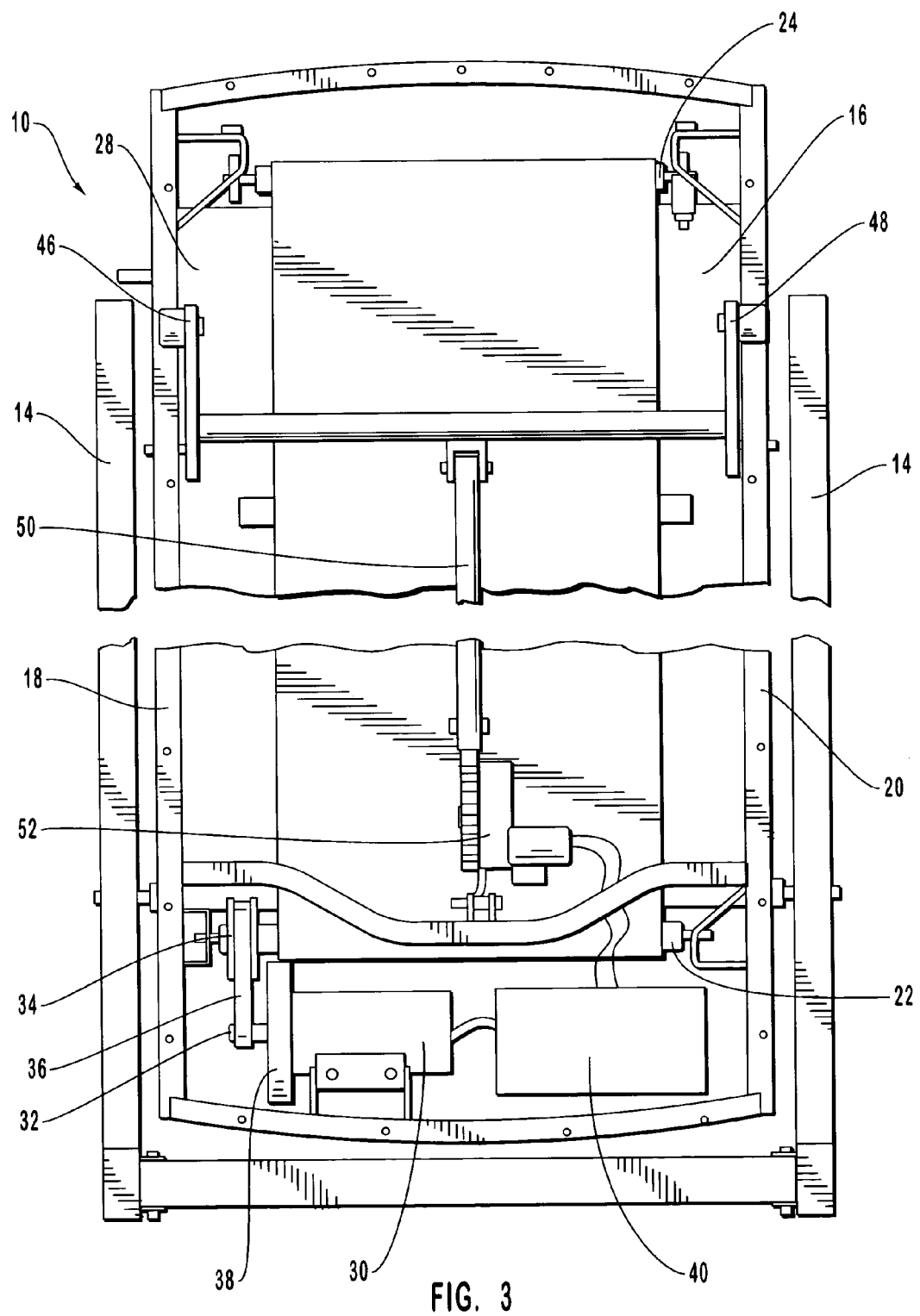
FIG. 3 is a partial plan view of portions of the reorienting treadmill illustrated in FIGS. 1 and 2 with the treadmill oriented in the second or storage position and with the bottom cover removed, revealing some of the internal components of the treadmill.

Referring now to FIGS. 1 through 4 generally, which depict a typical motorized, reorienting treadmill 10. Treadmill 10 includes a control panel 12 supported on a generally upright support structure 14 and a tread base 16. The tread base 16 typically includes a pair of side rails 18 and 20, a front pulley 22 and a rear pulley 24 disposed between and supported by the side rails 18 and 20, and a continuous belt 26 extending between and around front and rear pulleys 22 and 24. A deck 28 typically supports the upper run of belt 26. As best seen in FIG. 3, front pulley 22 is mechanically coupled or linked to an electric tread drive motor 30 by way of pulleys 32, 34, and a drive belt 36. Motor 30 also incorporates an inertial flywheel 38 and is electrically coupled or linked to a treadmill controller 40. The operation of motor 30, and thus the speed of belt 26, is controlled by treadmill controller 40, either in response to direct input by the user through various input devices 42 (e.g., switches, rheostats, etc.) located on control panel 12 or in response to programming stored in volatile or nonvolatile memory incorporated into treadmill controller 40. As will be discussed in later Figures, input devices 42 can also include a wireless receiver or transceiver component (not shown) for receiving infrared control signals, Bluetooth radio packets, or other types of wireless signals, etc. Visual indicators relating to the operational status of treadmill 10, such as speed, inclination, duration of the work out, etc., are provided to the user through one or more output devices 44 located on control panel 12. Typical output devices 44 include, but are not limited to, light emitting diode (LED) displays and/or liquid crystal displays (LCD).

Figure 4:
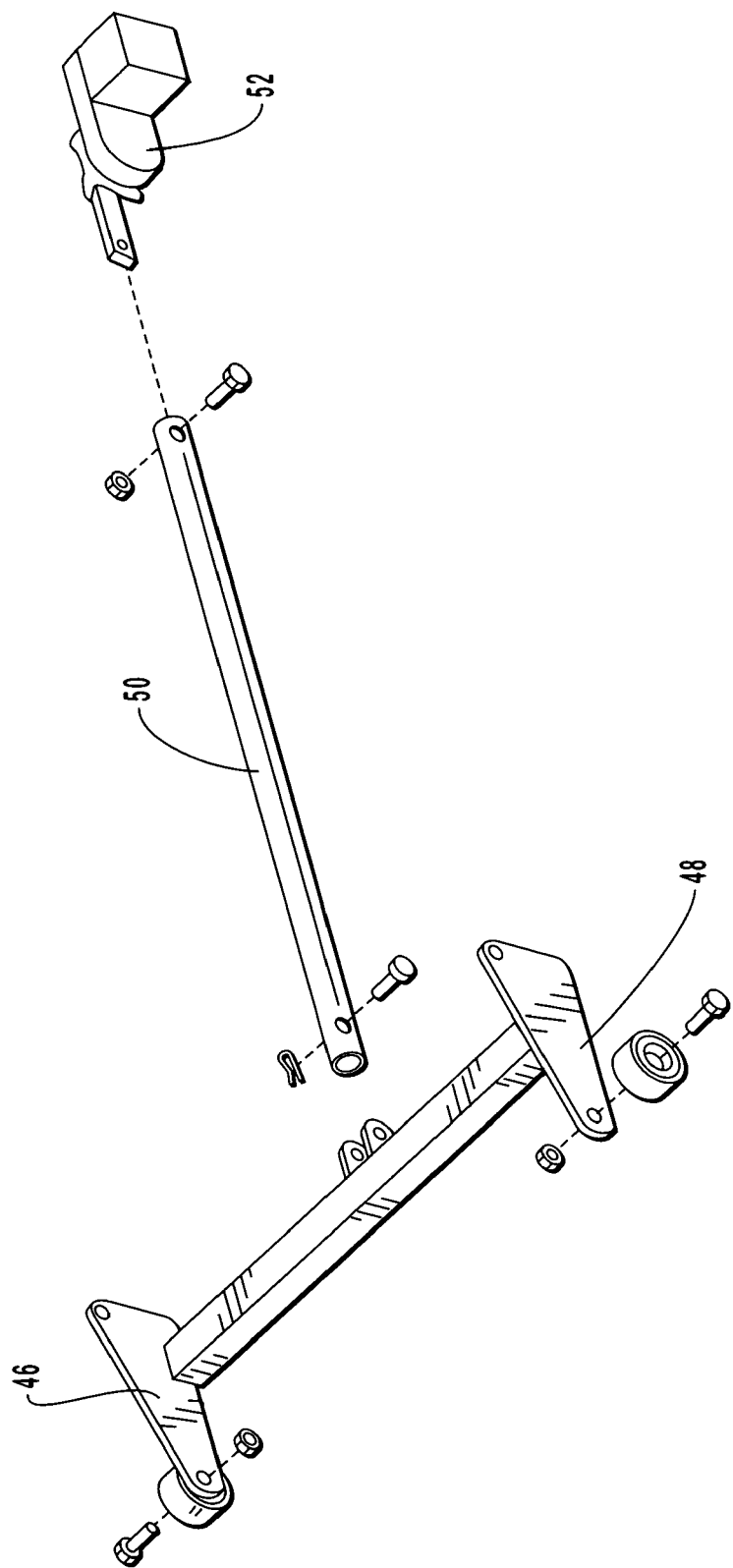
FIG. 4 is a partial exploded perspective view of the inclination mechanism incorporated into the treadmill illustrated in FIGS. 1 through 3.

In addition to the ability to control and vary the speed of belt 26, treadmill 10 also permits the degree of inclination of tread base 16 relative to the floor to be varied. Typically, this is accomplished through the use of an inclination drive motor that raises or lowers one end of tread base 16 relative to the other end. In the embodiment illustrated in FIGS. 1 through 4, a pair of rear feet 46 and 48 are rotatably attached to the rear of portion of side rails 18 and 20. As best seen in FIGS. 3 and 4, feet 46 and 48 are also mechanically coupled or linked through a shaft 50 to an inclination drive motor 52, which causes feet 46 and 48 to pivot about their points of pivotal attachment to side rails 18 and 20, thereby selectively raising or lowering the rear end of tread base 16 relative to the front end thereof. Motor 52 is also electrically coupled or linked to, and controlled by the treadmill controller 40, such that it can be manipulated in response to, for example, an input device 42 that takes wireless control signals received through a wireless receiver component, an input device 42 that takes direct user input through a device located on control panel 12, or to programming stored in volatile or nonvolatile memory incorporated into treadmill controller 40.

Again, neither the particular exercise device nor the particular design of a given exercise device is intended to limit the scope of the present invention. Rather, the present invention has broad application for any number of exercise devices known to those skilled in the art.

In the present invention, programming is used that contains both motivational content and one or more control signals. The control signals are synchronized with the motivational content and are designed to control one or more operating parameters of the exercise device, such as treadmill 10, in synchronization with the motivational content. As used herein, the term "motivational content" is used to broadly refer to any audio material, including dialog, narration, sound effects and/or music, either alone or in combination with video material. In one embodiment of the present invention, the motivational content includes an audio/video presentation of a personal trainer and others engaged in a series of exercises of varying difficulty using treadmills or other exercise devices. The motivational content includes voice-overs by the trainer, including dialog designed to instruct and encourage the user of treadmill 10, and accompanying background music. The tone and tempo of both the dialog and the background music is selected to match the intensity of the workout. While the foregoing selections are provided by way of example, it should be understood that the selection of the particular audio and video used to motivate and inspire the user of treadmill 10 is virtually limitless and is left to the imagination of the producer of the motivational content.

As mentioned above, the programming also contains control signals for controlling one or more operational parameters of the exercise device. In the case of treadmill 10, the programming includes control signals that control the speed of belt 28, as well as signals that control the degree of inclination of tread base 16. Furthermore, the control signals are synchronized with the motivational programming such that the intensity of the operation of treadmill 10 coincides with the intensity of the motivational content of the programming, and vice versa.

The programming may be either performed live or prerecorded. Whether live or prerecorded, programming incorporating audio and video can be transmitted via existing broadcast technology, including television broadcast over the airwaves, via cable, via satellite, via telephone lines, via the internet, via wireless technologies, via IR technologies, combinations thereof, or any other suitable transmission technology or medium. Similarly, programming containing only audio can be transmitted via existing radio broadcast technology, including over the airwaves, via cable, via satellite, via telephone lines, via the internet, via wireless technologies, via IR technologies, combinations thereof, or any other suitable transmission technology or medium. In this way, some embodiments of the present invention are compatible with existing conventional broadcast technologies and can interface with existing audio and/or video components commonly found in homes, thereby reducing the overall cost of the exercise device. Other embodiments use existing broadcast technologies to distribute programming to a general location of one or more exercise devices, while dedicated audio and/or video components deliver the programming to one or more exercise devices.

The programming may also be prerecorded and stored on a suitable storage medium. Any form of storage medium that is suitable for storing audio and/or video signals or data can be used and is within the scope of the present invention. For example, programming that contains only audio can be stored on audio cassette tapes, compact discs (CDs), mini-discs (MDs), computer diskettes or any other storage media suitable for storing audio programming. Similarly, programming that contains both audio and video can be stored on videotapes, laser discs (LDs), digital video discs (DVDs), computer diskettes or any other storage media suitable for storing audiovideo programming.

The present invention also includes means for reproducing the programming. The particular reproducing means is selected based on either the manner in which the programming is transmitted (e.g., television or radio signals) or the storage media on which the programming is stored (e.g., tape player for audio tape, CD player for CDs, MD player for MDs, VCR for videotapes, LD player for LDs, DVD player for DVDs, personal computer for computer diskettes, etc.). In addition, the reproducing means can either be separate and distinct from treadmill 10 (as reflected in FIGS. 5 and 6) or, alternatively, the reproducing means can be integrated into treadmill 10 itself (as reflected in FIG. 7). The advantage with the former is that it enables treadmill 10 to interface and operate with existing audio and/or video components (e.g., televisions, home stereos, computers, etc.) that may already be found in the home and does not significantly increase the cost of treadmill 10. Another advantage with the former is that a central control center capable of producing audio/video programming from a storage medium can interface and operate with one or more different exercise devices.

The present invention also includes means, responsive to the control signals, for controlling the operation of treadmill 10. Where the reproducing means is separate and distinct from treadmill 10 (FIGS. 5 and 6), the control means includes sensor means for sensing and converting the audio portion of the reproduced programming to an electrical signal, means for decoding said control signals, and means for driving said one or more motors or other electrically driven actuators in response to the decoded control signal. In one embodiment, the sensor means is a condenser microphone incorporated into control panel 12 of treadmill 10. As the programming is reproduced by the reproducing means, the condenser microphone picks up the audio portion of the programming and converts or transforms the audio portion of the programming back into an electric signal. The output of the microphone is electrically coupled to decoder circuitry, which detects, separates out the control signals from the rest of the programming and interprets or decodes the control signals. The driving means, which is electrically coupled to the output of the decoder circuitry, drives the appropriate motors or actuators of treadmill 10 in response to the control signals received through the microphone as part of the programming.

In another configuration, the sensor means is a wireless or IR receiver incorporated into or detachedly connected to the exercise device. As the programming is reproduced, the wireless or IR receiver receives the programming and converts or transforms the audio portion of the programming back into an electric signal. The output of the picks up the audio portion of the programming is electrically coupled to decoder circuitry, which detects, separates out the control signals from the rest of the programming and interprets or decodes the control signals.

In either case, when the tempo of the motivational content increases, the programming will contain a control signal to increase the speed of main motor 26 which, in turn, increases the speed of belt 36. As discussed in more detail below, the control signals are superimposed on the audio signal of the motivational content and are picked up by the microphone. The decoder circuitry then distinguishes between the control signal and the audio portion of the motivational content (i.e., dialog, sound effects, music), interprets the control signals and then provides the appropriate control signals to the appropriate motor or actuator of treadmill 10. Where the reproducing means is integrated into treadmill 10 (FIG. 7), a sensor means or microphone is not required. Instead, the output of the reproducing means is directly, electrically coupled to the decoder circuitry.

The format for encoding the control signals will now be discussed. It should again be understood that the method of encoding set forth below is representative only and is not intended to limit the scope of this invention. Any number of encoding schemes, which are known to those skilled in the art, could be used to carry out, and are encompassed within, the scope of the present invention. In one embodiment, the control signals are carried on a 2 kHz carrier signal, with each control signal having two transmission bursts, each burst having three bytes of data. The second burst is intended to exactly duplicate the first burst for error checking purposes. The first byte of data of each burst indicates the desired speed of the treadmill, the second byte of data indicates the desired inclination of the tread base 16, and the third byte is a checksum of the first and second bytes. The control signals also use standard RS232 protocol. Each control signal, including both bursts, is typically less than one-quarter second in duration. Each byte can have 8 bits of data, giving a high degree of resolution for controlling treadmill speed and the degree of inclination. In one embodiment, each time a control signal is inserted into the programming, the control signal entirely suppresses the audio portion of the motivational content for the duration of the control signal. As a result, the control signals are audible to the user, which also provides an audible cue or warning to the user that one or more operating parameters of treadmill 10 is about to change. In other configurations, the audio portion of the motivational content is not suppressed.

As alluded to above, the control signals are detected and decoded by a control signal decoder, which verifies that the control signal has the proper 2 kHz carrier frequency, checks to make sure that the control signal is otherwise properly formatted, and checks for errors. The decoder then passes the appropriate control signals to the processor, which in turn controls the appropriate operating parameters of the treadmill or exercise device.

Reference is now made to FIG. 5, which is a functional block diagram of one embodiment of the invention, wherein the programming is transmitted from a location remote from treadmill 10. As alluded to above, the invention includes means for reproducing the programming and means responsive to control signals encoded in the programming for controlling one or more operating parameters of treadmill 10 in synchronization with the motivational content of the programming. In the embodiment illustrated in FIG. 5, the structure corresponding to the reproducing means is conventional broadcast transmission equipment or device 54 in combination with a conventional audio and/or video receiver and playback device 56. Where, for example, the programming is transmitted via a television signal, receiver and playback device 56 may include a conventional television. Where the programming is transmitted via a radio signal, receiver and playback device 56 may include a conventional radio or home stereo receiver. In any event, the audio portion of the programming is reproduced by receiver and playback device 56 through a speaker 58. The video portion, if any, of the programming is displayed by receiver and playback device 56 through a suitable video display 60, such as a CRT, LCD or other similar device suitable for displaying video.

The invention also includes means, responsive to control signals encoded in the programming, for controlling one or more operating parameters of treadmill 10 in synchronization with the motivational content of the programming, which includes (i) sensor means for sensing and converting the audio portion of the reproduced programming into an electrical signal, (ii) means for decoding the control signals, and (iii) means for driving one or more operating parameters of the exercise device in response to the decoded control signals.

In the embodiment illustrated in FIG. 5, the structure corresponding the sensor means includes a microphone 62, which is integrated into the treadmills 10, as part of control panel 12. Microphone 62 receives the reproduced programming in the form of acoustic sound waves produced by speaker 58 and converts the received acoustic signals into an electric signal. The output of microphone 62 is received by control signal decoder circuit 64, which includes the means for decoding the control signals. As discussed previously, decoder circuit 64 detects and identifies properly formatted control signals by checking for the proper 2 kHz carrier frequency and checking for errors by comparing the values of the first two bytes against the checksum contained in the third byte. Once decoder circuit confirms that a properly formatted control signal has been received, it then breaks down the control signal and separates out the speed control portion contained in the first byte from the inclination control portion contained in the second byte and passes the appropriate control signals to processor 66, which in turn adjusts the speed of tread motor 30 and/or the position of inclination motor 48 as dictated by the received control signal.

Figure 6:
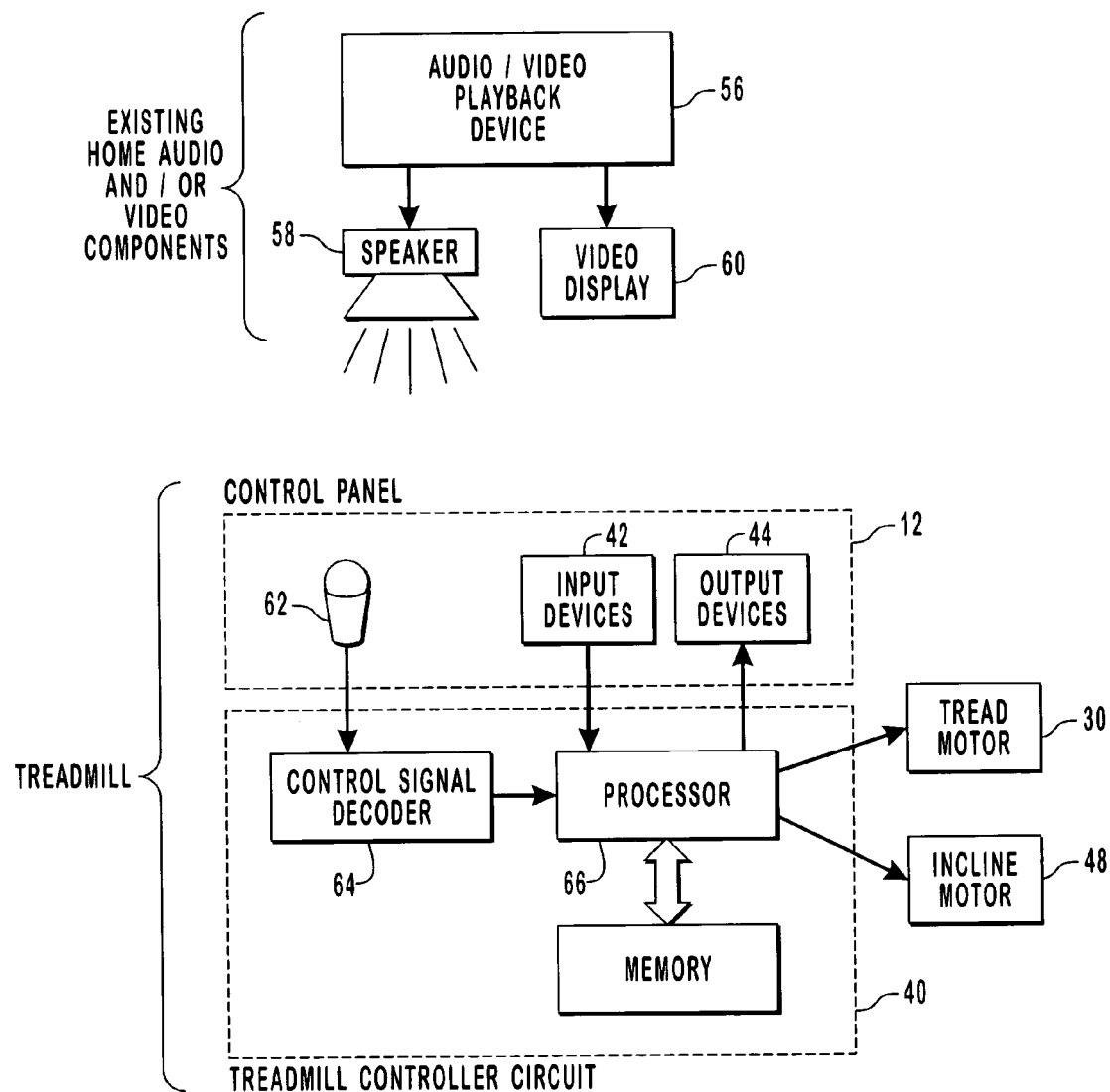
FIG. 6 is a functional block diagram of another embodiment of the present invention.

Reference is now made to FIG. 6, which is a functional block diagram illustrating another embodiment of the invention. The embodiment of FIG. 6 differs from that illustrated in FIG. 5 only in that it is intended to be used with programming that is stored on a player-readable storage medium, as opposed to be transmitted from a remote location via conventional broadcast channels. In this embodiment, playback device 56 is selected based on the type of storage media on which the programming is recorded or otherwise stored. In all other material respects, the embodiment illustrated in FIG. 6 functions essentially the same as the embodiment illustrated in FIG. 5.

Figure 7:
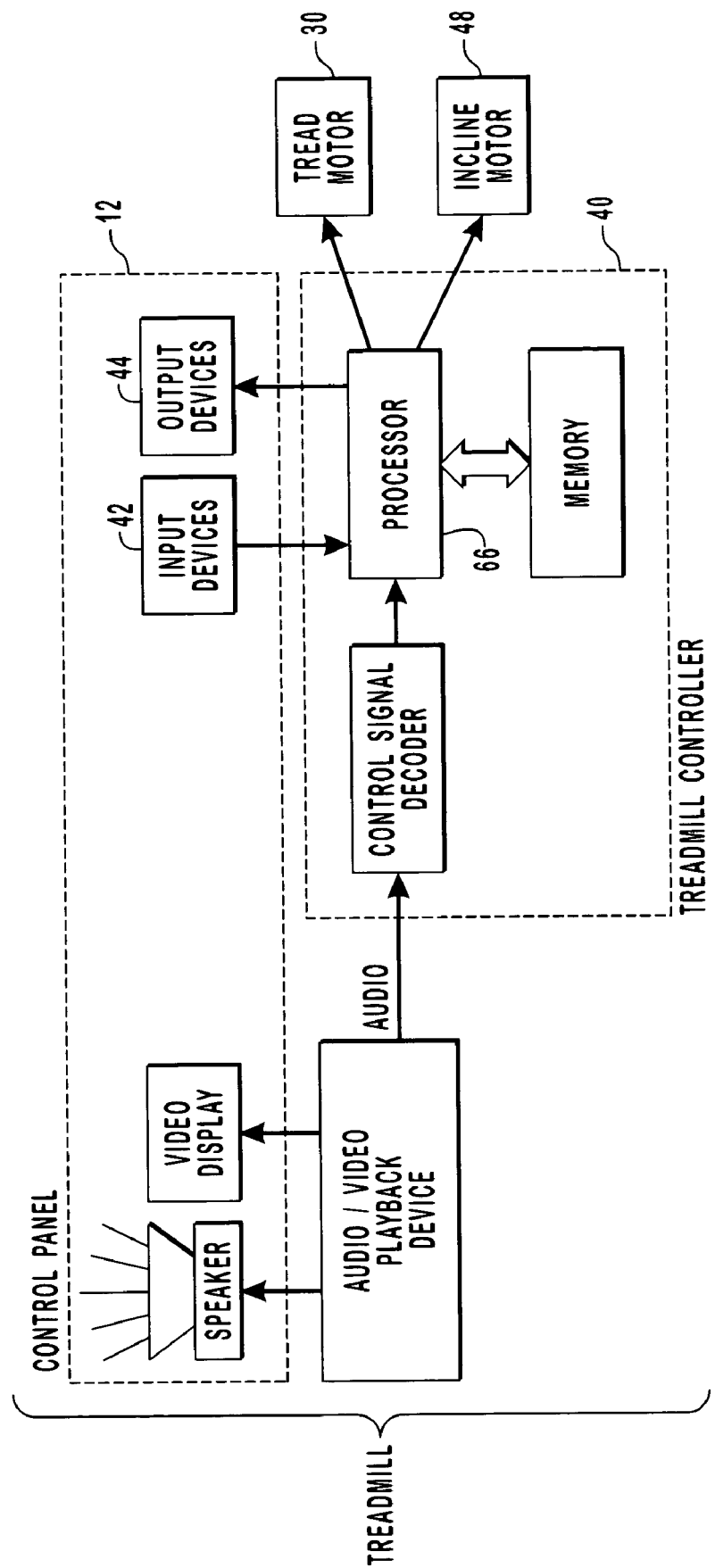
FIG. 7 is a functional block diagram of another embodiment of the present invention.

Referring now to FIG. 7, which is a functional block diagram of yet another embodiment of the invention. In this embodiment, playback device 56 is incorporated into treadmill 10, thereby eliminating the need for separate audio and/or video equipment. Where in the programming includes only audio, playback device 56 includes an audio cassette player, a CD player, a MD player or other suitable audio playback device that is compatible with the format on which the programming is recorded or otherwise stored. Similarly, if the programming includes both audio and video, playback device 56 includes a display suitable for displaying video images in combination with either a video cassette player, a DVD player or a LD player. The speakers 58 and/or video display 60 of the playback device 56 are incorporated into control panel 12 of treadmill 10.

The embodiment illustrated in FIG. 7 differs from the embodiments illustrated in FIGS. 5 and 6 in that it does not require the use of a separate sensor for sensing and converting the reproduced audio portion of the programming. Rather, the output of playback device is coupled not only to speaker 58 and/or video display 60, but is also electrically coupled to the input of control signal decoder circuit 64. In all other material respects, the embodiment illustrated in FIG. 7 functions essentially the same as the embodiment illustrated in FIG. 5.

While the embodiments illustrated in FIGS. 5 and 6 both contemplate the use of a speaker and microphone as the means of transferring the audio portion of the programming between receiver and playback device 56 and treadmill 10, it should be understood that other devices could readily be used to perform the same function. For example, an RF transmitter connected to receiver and playback device 56 and a compatible RF receiver connected to treadmill 10 could be used in place of speaker 58 and microphone 62. Similarly, an infrared transmitter and compatible infrared receiver could also be used to accomplish the same function.

Generally, therefore, the present invention is directed to improved methods of operating an exercise device consistent with the teachings set forth above. In accordance with the present invention, the method includes the steps of (i) producing programming having motivational content and one or more control signals for controlling one or more parameters of an exercise device, (ii) transmitting the programming to the exercise device, whether from a local control center or a remote control center through the local control center; (iii) receiving and reproducing the transmitted programming; (iv) decoding the control signals, and (v) adjusting operating parameters of the exercise device in response to the decoded control signals such that the operation of the exercise device is synchronized with said motivation content. The actions corresponding to each of the foregoing steps are the same as and consistent with the teachings directed to apparatus discussed in detail above.

FIGS. 8-13 illustrate yet other embodiments for practicing the present invention with particular regard to use of a central control unit 100 for controlling one or more exercise devices 110 through use of a wireless signal carrier, such as, but not limited to, infrared, radio transmission, Bluetooth, and any other wireless digital and analog carrier signals. Although reference is made herein to central control unit 100 using wireless signal carrier or wireless signals to control one or more exercise devices 110, it will be understood by one skilled in the art that similar control can occur through signal propagating along a wired or hardwired connection between central control unit 100 and one or more exercise devices 110. This wired connection can include, but not limited to, conductive wires or optical fibers.

Figure 8:
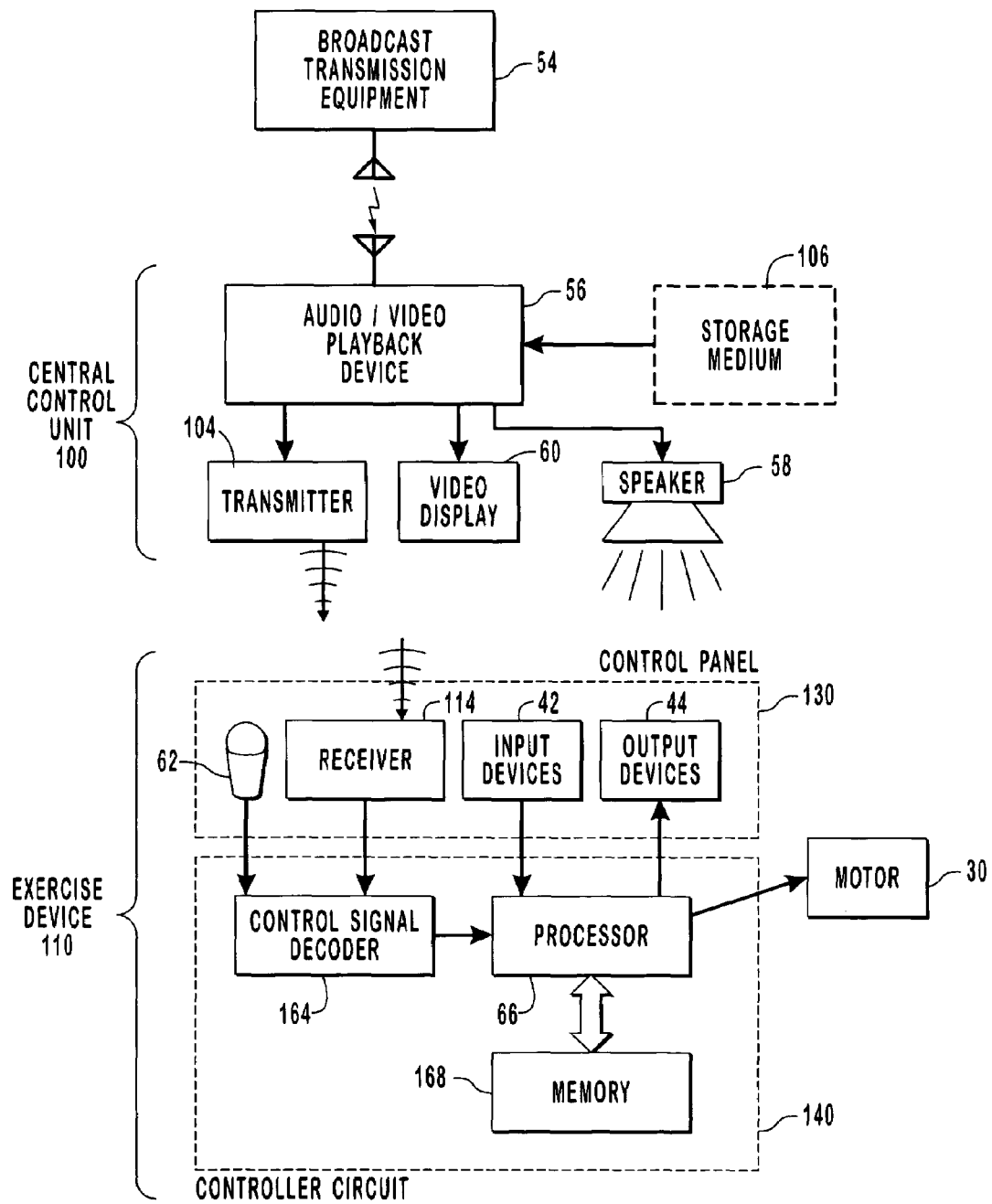
FIG. 8 is a functional block diagram of yet another embodiment of the present invention.

As shown in a generalized block diagram representation of one embodiment of the present invention, central control unit 100 cooperates with one or more exercise devices 110, only one being depicted in FIG. 8, which can be of a similar or dissimilar type. For instance, central control unit 100 can control the operation of one or more aerobic exercise devices, one or more anaerobic exercise devices, or a combination of both aerobic and anaerobic exercise devices. The central control unit 100 can be an existing home audio and/or video system or a custom audio and/or video system dedicated to delivering programming that includes motivational content and/or control signals. Central control unit 100, either alone or in combination with one or more of exercise devices 110, therefore functions as means for reproducing the programming. Additionally, exercise device 110, whether as a whole or one or more components thereof, can function as means, responsive to wireless control signals encoded in the programming, for controlling one or more operating parameters of an exercise device in synchronization with the motivational content. Greater detail of such means and associated structures is provided hereinafter.

As shown in FIG. 8, central control unit 100 includes audio/video playback device 56 that broadcasts programming received from broadcast transmission equipment or device 54 or from a storage medium 106. The broadcast transmission equipment 54 can be equipment or devices that broadcast exercise programming, including motivational content and/or control signals, via television broadcast over the airwaves, via cable, via satellite, via telephone lines, via the internet, via wireless technologies, via IR technologies, combinations thereof, or any other suitable transmission technology or medium. Consequently, central control unit 100 can re-broadcast or relay received exercise programming to one or more exercise devices 110.

To aid with broadcasting the exercising programming received directly from broadcast transmission equipment 54, storage medium 106, or a combination of the two, a transmitter 104, a video display 60, and/or a speaker 58 of central control unit 100 broadcasts the programming to exercise device 110 and optionally the user of exercise device 110. Although video display 60, speaker 58, transmitter 104, storage medium 106, and broadcast transmission equipment 54 are illustrated as being separate from audio/video playback device 56 one skilled in the art will understand that one or more of the same can be incorporated within audio/video playback device 56.

Transmitter 104 cooperates with audio/video playback device 56 and broadcasts or delivers received programming to exercise device 110. Transmitter 104 can be an omni-directional or a directional transmitter, i.e., broadcast a wireless control signal to one or more exercise devices 110 equipped with a corresponding receiver 114 or broadcast a wireless control signal to a single exercise device 110 at one time. This transmitter 104 can have structures appropriate for the particular type of electromagnetic wave to be transmitted to exercise device 110 and the type of connection between central control unit 100 and one or more exercise devices 110 i.e., wireless or wired connection. For instance, when using an IR signal, transmitter 104 includes photo-diodes and other circuitry to transmit an IR signal modulated with the control signals. Similarly, when using an RF signal, transmitter 104 includes RF circuitry to transmit an RF signal modulated with the control signals. Further, when using a signal capable of propagating along an optical fiber or conductive fiber associated with a wired connection, transmitter 104 can include appropriate optical and electrical circuitry to enable delivery of exercise programming to one or more exercise devices. The signal modulation can be frequency, amplitude, or wavelength modulation.

One will appreciate that the programming delivered by transmitter 104 can include the motivational content and/or the control signals. As mentioned above, video display 60 and speaker 58 are optional. Therefore, central control unit 100 can deliver programming to exercise device 110 through a "silent" wireless connection, i.e., exercise device 110, alone or in combination with separate video display and/or speakers electrically connected to exercise device 110, delivers programming to the exercising user rather than central control unit 100 delivering the programming to the exercising user.

The programming deliverable to exercise device 110 by transmitter 104 is received from broadcast transmission equipment 54 or storage medium 106. By way of example and not of limitation, storage medium 106 can include any type of internal or external storage media, whether volatile or non-volatile storage and whether or not such storage is removable from central control unit 100. The storage medium 106 can, therefore, include Random Access Memory (RAM), Read Only Memory (ROM), and other types of nonvolatile storage such as "flash memory". The storage medium 106 can also include optical disc storage such as Compact Disc Read Only Memory (CDROM), Compact Disc Rewritable (CDRW), and Digital Versatile Disc (DVD), etc.). The storage medium 106 can further include any hard disk storage that connects via a Small Computing System Interface (SCSI), through an internet Small Computing System Interface (iSCSI), through a Universal Serial Bus (USB), and/or through an IEEE 1394 interface (Firewire).

This storage medium 106 accommodates various types of programming, including motivational content and/or control signals. Users of the present invention can receive different programming by purchasing different storage media, such as through retail stores, the Internet, catalogs, or other vendor that provides a physical storage media to the user. Alternatively, users can access electronic versions of programming through the Internet or other communication connection. In this case, the programming is downloaded directly to audio/video playback device 56 and/or storage medium 106, whether storage medium is fixably or removably mounted to central control unit 100.

In addition to central control unit 100, the present invention further includes exercise device 110 that can be an aerobic or anaerobic exercise device. Exercise device 110 includes structures and components that facilitate capturing or receiving of the programming, whether only control signals, only motivational content, or a combination of both motivational content and control signals. This capturing or receiving structure or component can be a receiver 114 mounted to or removably attached to exercise device 110. Receiver 114 is complementary to transmitter 104, so that when transmitter 104 is an RF transmitter, receiver 114 is an RF receiver. Similarly, when transmitter 104 is an IR transmitter, receiver 114 is an IR receiver. Further, when a wired connection is used to deliver programming to exercise device 110, receiver 114 can be optical and/or electrical components capable of receiving signal that propagate along an optical fiber or conductive wire. In other embodiments, transmitter 104 and receiver 114 are "transceivers", i.e., structures or components that function to transmit data and receive data.

The receiver 114 can attached to or be integrally formed with a control panel, identified by numeral 130, or other portion of exercise device 110. The control panel 130 can have a similar configuration to the other control panels described herein, such as control panel 12. Consequently, control panel 130 can include one or more input devices 42, one or more output devices 44, and a microphone 62. The function and structure of such devices 42, 44 and microphone 62 were discussed in detail previously. These devices 42, 44, microphone 62, and receiver 114 electrically communicate or electrically connect with controller circuit 140. As with the other control circuits of the present invention, i.e., control circuit 40, controller circuit 140 manages the operation of one or more motors 30. For instance, when exercise device 110 is a treadmill, controller circuit 140 manages the operation of a tread belt motor that moves a tread belt and/or an incline motor that varies the angular orientation of the tread.

In the embodiment illustrated in FIG. 8, control signal decoder 164 receives the output of receiver 114. Control signal decoder 164, and its associated circuitry, includes and functions as one exemplary configuration of means for decoding the control signals. Decoder 164 functions similarly to decoder 64, by detecting and identifying properly formatted control signals. In an exemplary configuration, these control signals are within wireless signals. In one embodiment related to a signal for a treadmill, the control signals have two transmission bursts, each burst having three bytes of data. The second burst is intended to exactly duplicate the first burst for error checking purposes. The first byte of data of each burst indicates the desired speed of the treadmill, the second byte of data indicates the desired inclination of the tread base, and the third byte is a checksum of the first and second bytes.

In other configurations, the format of the signal may be different. No matter the particular format of the signal, decoder 164 confirms that a properly formatted, wireless control signal has been received and subsequently breaks down the wireless control signal and separates out the control portions. These portions are used by processor 60 to change the operation of motor 40, with an option to store the control signals with the motivational content in a memory 168.

To aid in controlling the operation of multiple exercise devices and multiple types of exercise devices, each burst of data can optionally include a frame, header, or additional byte(s) that identify the type of exercise device to receive the control signal. By so doing, central control unit 100 can broadcast exercise programming that controls different types of exercise device during an exercise routine associated with the exercise programming. For instance, an exercise program can warm-up an exercising user using a treadmill and control an anaerobic training session using a weight stack. In this case, central control unit 100 broadcasts the programming to the exercise devices near central control unit 100, i.e., the treadmill and the weight stack. The controller circuitry 140 of each exercise device analyzes the received control signals to identify the type of exercise device for which the signals relate. When control signal decoder 164 and processor 66 identify control signals specific to that exercise device, processor 66 changes the operation of motor 30 based upon the received control signals. In this example, both the treadmill and the weight stack receive all control signals and all motivational content, but the treadmill will operate with control signals having a treadmill-specific frame, header, or additional byte(s) and the weight stack will operate with control signals having a treadmill-specific frame, header, or additional byte(s). In another configuration, however, central control unit 100 can analyze the control signals to identify the exercise-specific frame, header, or additional byte(s) and deliver those control signals to only the exercise device to be controlled by those control signals. For instance, central control unit 100 can identify treadmill-specific control signals and deliver those treadmill-specific control signals to the treadmill.

Figure 9A:
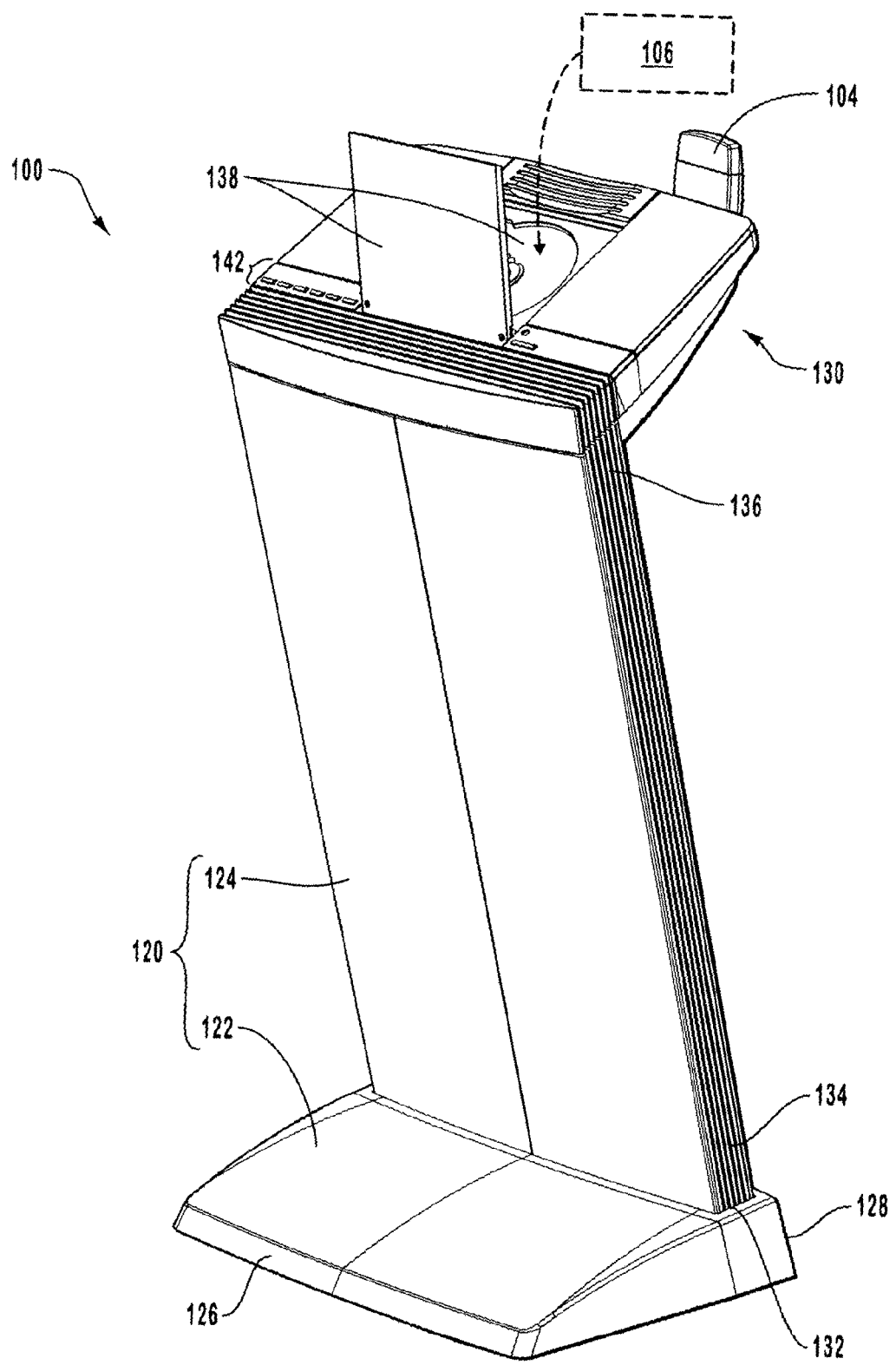
FIGS. 9A-9B illustrate perspective views of an exemplary central control unit in accordance with one embodiment of the present invention.
Figure 9B:
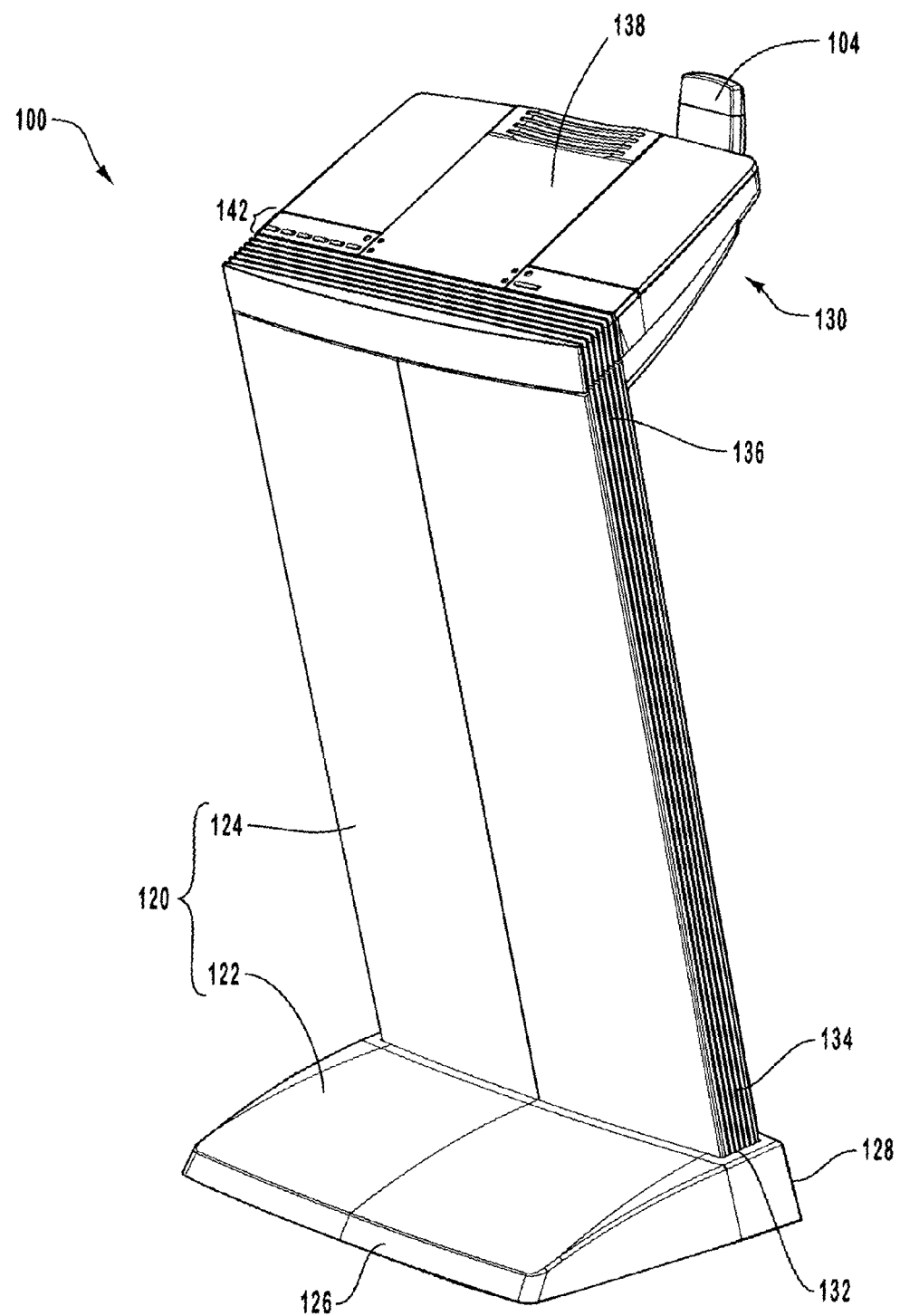

FIGS. 9A-9B illustrate two perspective views of central control unit 100 for use with the present invention. With reference to FIG. 9A, central control unit 100 has a receptacle 120 that supports storage medium 106. The receptacle 120 has a base 122 upon which is mounted a stand 124. The base 122 provides a stable foundation to central control unit 100, and aids in preventing tipping or other unwanted movement of central control unit 100 during use. In the illustrated configuration, base 122 includes a generally tapered configuration that extends from a first edge 126 to a second edge 128. Although this is one configuration, one skilled in the art will appreciate that base can have any configuration or cross-section so long as the base aids with providing a stable foundation to central control unit 100.

Mounted to base 122 is a first end 134 of stand 124. First end 134 mounts within a channel 132 formed in base 122. One or more fasteners (not shown) can attach stand 124 to base 122. Alternatively, friction fits, thermal or chemical bonds, adhesives, or other techniques, either alone or in combination with one or more fasteners, attach stand 124 to base 122.

As shown, stand 124 extends from base 122 at an angular orientation relative to the surface upon which central control unit 100 is to rest. Disposed at a second end 136 of stand 124 is control panel 130. The angular orientation of stand 124 relative to base 122 aids in providing stability to the structure of central control unit 100 due to the weight of control panel 130 being disposed at second end 136 of stand 124. Although stand 124 is angularly orientated relative to base 122, stand 124 can be perpendicular to base 122 and/or a surface upon which central control unit 100 is to rest.

The control panel 130 mounted to second end 136 of stand 124 provides the input and output controls and indicators that enable a user to broadcast programming to one or more exercise devices. The control panel 130, as shown in FIG. 9A, includes an input receptacle 138 that can open or close for accepting input media, such as storage medium 106. FIG. 9A illustrates input receptacle 138 in an open state, while FIG. 9B illustrates input receptacle 138 in a closed state.

This input receptacle 138, as shown in FIG. 10, is generally any device (whether connected through an internal or external connection interface) that can play or access the programming or exercise programming stored upon storage medium 106 (FIG. 9A). Therefore, input receptacle 138 can be a magnetic hard disk drive for reading from and writing to a magnetic hard disk, a magnetic disk drive for reading from or writing to a removable magnetic disk, and an optical disc drive for reading from or writing to removable optical disc, a media stick reader for reading from or writing to a removable flash memory card or stick. In the illustrated configuration, input receptacle 138 is a compact disc tray, and can further include one or more input ports for attaching various storage media (already described).

In addition to accommodating removable media, the term "input receptacle" can include the ports and connectors that facilitate delivery of programming to a hard disk drive mounted or supported by control panel 130 and generally programming received by central control unit 100 such as from broadcast transmission equipment 54 (FIG. 8). For instance, central control unit 100 (FIG. 9A) can include, at any location thereof, one or more Audio-In (e.g., using RCA or other standard audio jacks), USB, Firewire, Ethernet, serial, SCSI ports, wireless ports, or other wired ports to receive programming and/or deliver programming. (FIG. 8). More generally, central control unit 100 can include a physical network link (not shown), such as through a telephone or Ethernet cable, and circuitry (not shown) for receiving and interpreting data received over such a link. Thus, an input receptacle can be configured to receive data directly from a storage medium separate from central control unit 100, or from a separate portable device that itself receives data from a storage medium, and then transmits the received data to central control unit 100 through an input receptacle.

For example, an input receptacle of central control unit 100 can include an Audio-In port for receiving a hardwired or wireless audio data line from a computerized output device, such as a portable output device. A portable output device can include, but is not limited to, such devices as a portable compact disc player, a portable MP3 player, a portable DVD player, a portable tape player, a portable analog or digital radio (including satellite-transmitted radio) player, a portable video player, or any combination of the above, or any other portable device that can output audio signals, video signals, or a combination of audio and video signals. A computerized output device can also include typically non-portable (or less-portable) computerized systems such as, but not limited to, a desktop computer, a laptop computer, a portable video player, and so on. In any such case, a user can attach one end of a reciprocal data line from, for example, a headphone jack (or other data line) on the computerized output device and attach the other end into an Audio-In port (or other related data line) of a complementary input receptacle. Alternatively, a user can attach wireless transmitters, receivers, or transceivers to the computerized output device and central control unit 100 to deliver the programming from the output device to central control unit 100. In addition, it will be appreciated that the computerized output device itself can receive content from another source, such as storage medium, a general data transfer interface, broadcast transmission equipment, or, for example, streamed over a network connection. The computerized output device can then send the received content on to the input receptacle concurrently as the content is received from the other source, or after all the content has been completely delivered from the other source to the computerized output device.

Mounted to control panel 130 is a transmitter 104 that functions as a wireless transmission source. This transmitter 104 is either removable attached to control panel 130 or manufactured as an integrated whole. As discussed earlier, the type or configuration of transmitter 104 depends upon the format of the electromagnetic wave used to carry the control signals to exercise device 110. Therefore, transmitter 104 can be an IR transmitter, and RF transmitter, a transmitter that accommodates a hardwired connection between central control unit 100 and exercise device 110, or some other types of transmitter.

The transmitter 104 can include a sending portal 144, such as one or more IR portals, RF portal, or other wireless-type portals. Alternatively, a transceiver can be substituted for transmitter 104, i.e., a structure that can both transmit and receive signals. The transceiver would, therefore, have both a send portal and a receive portal. Having both sending and receiving portals can be of particular use where central control unit 100 is intended to keep a log of a user's progress, or adjust a workout program in sync with a user's present performance.

The central control unit 100 can also include input/output controls 142 that enable inputting of operating parameters. For instance, controls 142 can be used to distribute content found on the various storage media, control volume, control playback speed, skipping content in a forward or reverse direction, rewind, fast forward, pause, repeat, transmit, receive, upload, download, etc. These controls 142 can include touch sensitive buttons, rheostat-type buttons, switch-type buttons, or other buttons or controllers that enable a user to make selections of one or more operating parameters of central control unit 100. Output indicators 146 associated with input/output controls 142 can include a certain light display that blinks at various interval. For instance, the blinking can be coordinated or in sync with the motivation content, random, coordinated or in sync with certain beats of music, etc. This blinking provides a visual indication of the status of central control unit 100 and broadcasting of programming. Various visual indicators are known to those skilled in the art.

Generally speaking, control panel 130 can contain much of the active circuitry (not shown) used for receiving or sending control signals, as well as circuitry (not shown) for driving audio components such as speakers, i.e., the control circuitry schematically illustrated in FIG. 8. In other embodiments, much of the active circuitry (not shown) can be distributed throughout base 122 and stand 124 as needed.

Further, although reference has been made to control panel 130, and more generally central control unit 100 having transmitters, transceivers, input/output controls, lights, etc, one skilled in the art will appreciate that control panel 130 can include various other structures. For instance, control panel 130 can include one or more speakers, an air filter, an air purifier, a fan, a television display, a liquid crystal display, some other video or visual display, and other components.

Figure 11:
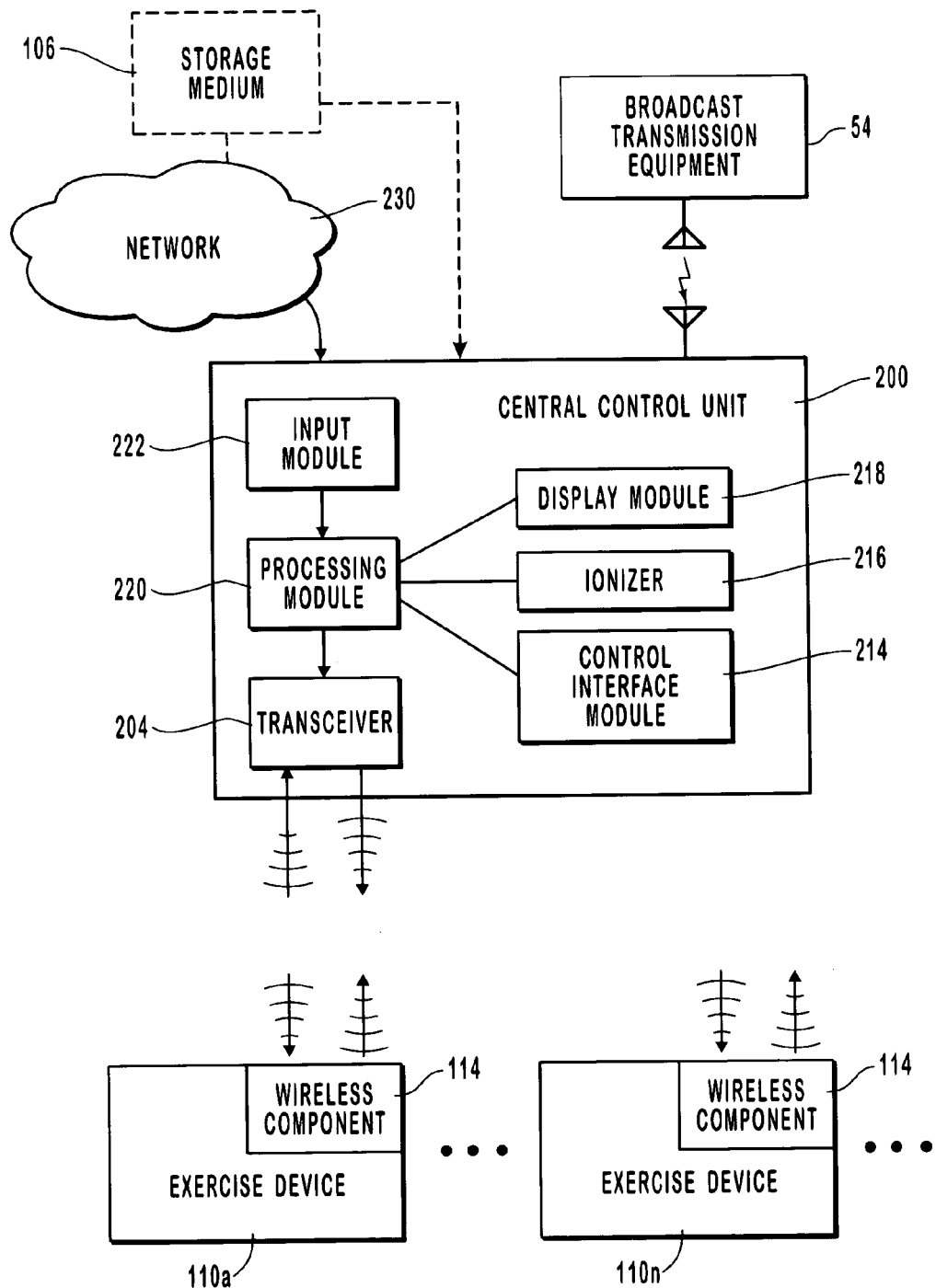
FIG. 11 is a block diagram illustrating one or more components that can be used in accordance with the present invention.

FIG. 11 illustrates a schematic block diagram of another exemplary central control unit, identified by reference numeral 200. It is understood that the features and functions of central control unit 100 also apply to central control unit 200 and vice versa. For instance, the following discussion relates to wireless connections between central control unit 200 and exercise devices 110*a*-110*n*, although one skilled in the art will understand that central control unit 200 can be hardwired to or wirelessly connected to exercise devices 110*a*-110*n*, storage medium 106, an output device, and/or broadcast transmission equipment 54.

The central control unit 200 has one or more active components and cooperates with one or more exercise devices 110*a*-110*n*. Generally, central control unit 200 for use with the present invention can include one or more components that are operated through a processing module 220. The processing module 220 can include one or more active circuitry components for processing executable instructions, such as a central processing unit, a host controller, or similar microprocessor.

As shown, processing module 220 can receive and process electronic data received from an input module 222. For instance, processing module 220 can execute machine-executable instructions stored at central control unit 200 or accessible by central control unit 200, including but not limited to, executing instructions that result in data being converted, manipulated, encrypted, translated, forwarded, relayed, changed to a wireless signal, changed to a signals capable of propagating along an optical fiber, changed to a signal capable of propagating along a conductive wire, or otherwise other processed in any manner. The input module 222 represents a combination of a physical and software interface, such as a set of routines or applications that receive data through a physical or wireless connection or portal, such as those described herein, and can read, manipulate, or translate the received signal. More generally, input module 222 receives the data through the physical or wireless connection and can forward the received data to processing module 220. As well, input module 22 can process portions of the received data (e.g., convert the received data into information that the processing module can understand) and forward processed and unprocessed portions of the data to the processing module 220, and so forth.

The processing module 220 can receive the data and perform functions based upon the data. For instance, processing module 220 can manipulate data representative of exercise programming, such as motivational content and/or control signals, and deliver all or a portion of the exercise programming to transceiver 204 for transmitting to exercise devices 110*a*-110*n*. Alternatively, processing module 220 manipulates the data and subsequently operates other structures or initiates other functions of central control unit 200. For instance, processing module 220 can use the data to (i) operate a display module 218 to display instructions, motivational content, control signals, or other information to an operator of central control unit 200, (ii) control the operation of an ionizer 216, with associated ionizer module, to filter air in a general vicinity of central control unit 200, (iii) access a removable or fixably attached storage medium 106, (iv) operate a control interface module 214 having associated user operated buttons or other selectors that aid a user in selecting workout programs, length of programs, volume of content, and so on, or (v) initiate other functions of central control unit 200.

Processing module 220 can also process instructions stored in a memory (not shown) of central control unit 200, whether volatile or nonvolatile memory, which are factory defined instructions or instructions received through control interface module 214 and/or transceiver 204. Processing of these instructions can occur without regard to whether central control unit 200 receives exercise programming through input module 222.

As mentioned above, processing module 220 can connect, for example, to display module 218. The display module 218 can include a cathode ray tube (CRT) display, a liquid crystal display (LCD), a plasma display, or some other video or visual display, with associated control circuitry. Programming, motivational content, data indicative of what programs are running, what programs may be next in line, or may allow further selection to find processed data based on prior workout routines. In an alternative embodiment, display module 218 can also indicate user's workout progress, based upon the time that the programming is broadcast or based upon data transmitted back by the exercise device during a workout routine. The display module 218 can also include one or more output components allowing a connection to a separate display device (not shown) through, for example, a common serial, RCA, component cable, and/or s-video connection. Thus, for example, if received input data includes certain video content along with the motivational audio content and control signals, some of the video content data can be output to a display device that is connected to one or more of the output components.

As illustrated in FIG. 11, input module 222 provides multiple means for receiving input. For example, central control unit 200 can include a connection to network 230. Through network 230 programming stored upon storage medium 106 can be downloaded or otherwise retrieved by central control unit 200. In one embodiment, the network connection can provide a direct connection to a specific Internet Protocol (IP) address, where a computer system at the IP address provides streaming exercise programming, including motivational content and/or control signals that input module 222 receives and processing module 220 processes. Alternatively, or in addition to, central control unit 200 can receive input from storage medium 106. In still another configuration, input module 22 receives input from broadcast transmission equipment 54. In at least one embodiment, a user can provide motivational content data to central control unit 200, where the user has received the content via a manufacturer-provided compact disc, or the user can plug in a flash memory card into a flash memory reader at central control unit 200. A transceiver 204 can also receive input data in the form of a return or feedback signal (e.g., a wireless or hardwired transmission of a user's progress on an exercise device) that can be processed at processing module 220.

The processing module 220 receives input and processes the input in a variety of different ways. For example, processing module 220 can take the received exercise programming from storage medium 106 or from broadcast transmission equipment 54 and interpret one or more data fields in the content as control signals and one or more other data fields as motivational content. Upon encountering control signals in the input data, processing module 220 converts the control signals into data that can be broadcast by transceiver 204, which can function as transmitter 104. In another configuration, processing module 220 receives two different groups or packets of data, one for motivational content and one for control signals; processing module 220 converting the control signals and/or the motivational content for broadcasting by transceiver 204. In still another configuration, processing module 220 receives motivational content and interprets one or more data fields as the control signals. Subsequently, the control signals and/or motivational contents are broadcast to exercise device 110a-110n. In still another configuration, processing module 220 receives exercise programming from broadcast transmission equipment 54 and re-broadcasts or relays the exercise programming to exercise devices 110a-110a via transceiver 204. The processing module 220 can also process wireless data that are received from an exercise device 10a-10n by transceiver 204.

The ability of central control unit 200 to send and receive wireless signals allows central control unit 200 to send signals to one or more exercise devices 110a-110n, as well as user-specific or device-specific signals as appropriate. For example, central control unit 200 can send a single wireless signal through transceiver 204 such that any exercise device equipped with receiver 114 (FIG. 8) receives and optionally interprets the data. This can have particular application such as for certain workout classes where a single instructor may wish to set up a common workout routine for multiple students.

Alternatively, central control unit 200 can send one or more user-specific control signals at once so that exercise device 110a and exercise device 110n process different instructions. This can allow different users to have different workouts at the same time on different exercise devices 110a, 10n even though working from the same central control unit 200. Furthermore, this can allow different users to compete against each other, where each exercise device 110a-110n can send signals in the form of wireless digital signals, or a signal propagating along an optical fiber or conductive wire, to another exercise device to indicate progress that can show up on an exercise device display screen, or for example, to a central control unit which then adjusts an outgoing signal to a competing exercise device, can keep a log of relative progress, and so on. These return or feedback signals from one exercise device can be sent to one or more of the central control unit 200 and one or more other exercise devices. Generally, these return or feedback signals will include one or more data fields indicating, for example, a user's workout progress on the transmitting device, can be sent at the user's initiative, or in response to a control signal sent by the central control unit 200.

Accordingly, each exercise device 110a-110n that communicates with central control unit 200 has an attached or integrated receiver 114 (FIG. 8) that can receive the wireless control signals. As well, each exercise device 110a-110n that communicates with central control unit 200 has a component, such as control signal decoder 164 (FIG. 8), which can decipher the wireless control signals and send the deciphered control signals to a processing unit, such as processor 66 (FIG. 8). In the case of optical wireless signals, such as infrared signals, a transimpedance amplifier or avalanche photodiode can be used to translate the wireless optical signal into electronic data, which would then be sent to, for example, control signal decoder 64 or 164.

Figure 12:
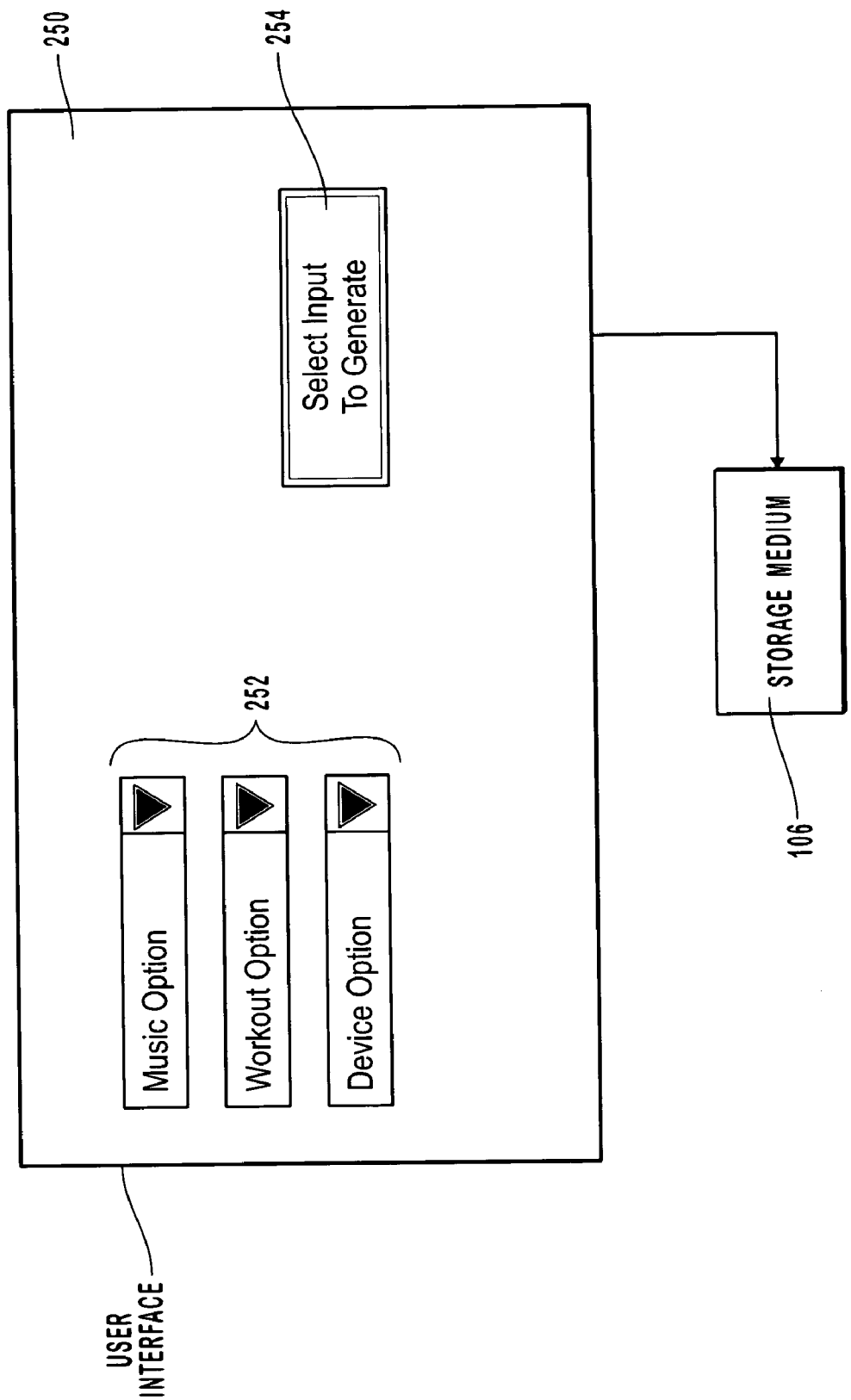
FIG. 12 illustrates a user interface that can be practiced in accordance with the present invention.

FIG. 12 illustrates at least one embodiment in which a user can receive user-specific motivational content that the user can input into the central control unit. In particular, rather than ordering generic motivational content from a content provider, the user can use a service provider to generate user-specific content. The service provider can be an application installed on the user's computer system (e.g., a desktop, laptop, or personal digital assistant computer system), or can be an application that a user logs-in to from a remote location over an Internet connection. In either case, the user can interact with a user interface 250 that provides the user with one or more options 252. For example, interface 250 can allow the user to select one or more different types of music, either remotely available, or found locally on the user's storage device. The interface 250 can also allow the user to select different types of workout options, such as a primarily anaerobic, or a primarily aerobic workout routine, a routine involving multiple speeds and changing resistances, a workout option that incorporates certain video content, or other types of motivational content and so forth. The interface 250 can also allow the user to select one or more device options in the option list 252, where the device options can indicate what types of equipment the user has available for use in a workout routine.

When the user has selected one or more of the options 252, the user can then select a generating or processing option 254. The generate option 254 instructs a computer system to execute one or more functional instructions, where the functional instructions can combine each of the one or more user choices into electronic data that represent a workout routine. In such a case, the generated workout routine data generally includes one or more motivational content portions, and one or more control signal portions that would be appropriate for the central control unit to broadcast to one or more other exercise devices, as selected by the user. Although, the workout routine can also include only motivation content, or only music content, such as one or more MP3 audio files that a user can input into the central control unit, without the benefit of control signals. In one embodiment, the generate option 254 can direct the combined output (workout routine data) through an Internet connection directly to the central control unit, or can send the output directly to a storage medium 106 that the user will download into the central control unit. For example, the output can be written to a USB or Firewire connected storage device such as a USB flash memory card, or can be written to a CDROM, a CDRW, a DVD, and so forth. In still another configuration, the generate option 254 can direct a remote service provider to create a storage medium with the defined exercise programming, this storage medium being delivered to the user via physical mail.

Accordingly, the exemplary embodiments of the present invention flexibly provide multiple options for the user to generate, store, and implement workout routines. This flexibility in sending wireless control signals can allow different users to implement user-specific workouts while hearing the same motivational content, or allow different users to compete against each other using the same workout and motivational content. Furthermore, this flexibility in using wireless control signals can allow similar benefits without restricting exercise equipment to certain physical locations (e.g., as dictated by a length of physical data wire to the control unit, or as dictated by floor space in multiple workout rooms, etc.).

From the foregoing description, it will be apparent that the present invention provides advantages and features not previously found in the prior art. For example, the present invention provides exercise devices that incorporate a standardized interface for receiving and decoding control signals embedded in multimedia programming for controlling various operating parameters of the exercise device in synchronization with the multimedia programming. In addition, the present invention provides home exercise devices that are capable of simulating a group or class workout environment and synchronizing operation of the exercises devices with motivational programming. The present invention also provides improved exercise devices, wherein programming containing motivational content and control signals can be reproduced using audio and/or video playback devices that are either custom devices or devices commonly found in the home, such as televisions, VCRs, home stereo equipment and the like, and the exercise device can decode and utilize the control signals to synchronize operation of the exercise device with the motivational content.

The present invention facilitates the use of interchangeable, multimedia programming that is external to the exercise device itself, making it possible to quickly and easily "program" the exercise device to perform an endless variety of exercise routines, accompanied by motivational content that is limited only be the imagination of producers of multimedia programming. The present invention also provides flexibility, in that the multimedia programming may be broadcast, either live or at a later time, from a location remote from the location of the exercise device or, alternatively, the multimedia programming can be recorded and/or stored on a suitable storage medium and reproduced at the convenience of the user.

Although multiple embodiments of the invention are described herein in detail, it will be understood by those skilled in the art that variations may be made thereto without departing from the spirit of the invention or the scope of the claims.

We claim:

1. A central control unit for controlling a plurality of exercise devices through wireless control signals delivered to the plurality of exercise devices, the central control unit comprising:
   a receptacle that supports at least one storage medium containing an exercise program to be delivered to the plurality of exercise devices, said exercise program comprising (i) motivational content and (ii) control signals synchronized with said motivational content; and
   a wireless transmitter communicably connected with said at least one storage medium and receiving said exercise program, said transmitter delivering said exercise program simultaneously to each of the plurality of exercise devices, wherein the central control unit is adapted to control an operation of a first exercise device of the plurality of exercise devices upon activation of the central control unit by a user and, upon completion of the operation of the first exercise device, automatically control an operation of a second exercise device of the plurality of exercise devices without any additional input from the user at the central control unit or at the plurality of exercise devices.

2. The central control unit as recited in claim 1, wherein said control signals are delivered to the plurality of exercise devices using at least one of an infrared signal and a radio signal.

3. The central control unit as recited in claim 1, wherein said receptacle further comprises a base, a stand extending from said base, and a control panel mounted to said stand.

4. The central control unit as recited in claim 1, wherein said receptacle further comprises an input receptacle that receives said at least one storage medium.

5. The central control unit as recited in claim 4, wherein said at least one storage medium comprises one or more of a magnetic storage medium, an optical storage medium, and a flash memory medium.

6. The central control unit as recited in claim 4, wherein said at least one storage medium stores one or more MP3 audio files.

7. The central control unit as recited in claim 1, further comprising at least one input port, said input port receiving said exercise program from a broadcast transmission device.

8. The central control unit as recited in claim 1, further comprising at least one input port, said at least one input port receiving said exercise program from a computerized output device.

9. The central control unit as recited in claim 1, wherein said receptacle further comprises at least one of a USB port, a Firewire port, an Ethernet port, a serial port, or a SCSI port.

10. The central control unit as recited in claim 1, wherein the simultaneous delivery of said exercise program to each of the plurality of exercise devices is the initial communication between the central control unit and each of the plurality of exercise devices.

11. The central control unit as recited in claim 10, wherein the initial communication is initiated by the user at the central control unit.

12. A central control unit for controlling a plurality of exercise devices through wireless control signals delivered to said plurality of exercise devices, the central control unit comprising:
    a support structure that rests upon a support surface;
    a control panel mounted to said support structure, said control panel comprising:
       an input receptacle that receives at least one storage medium containing a plurality of exercise programs to be delivered to said plurality of exercise devices, each of said plurality of exercise programs comprising (i) motivational content and (ii) control signals synchronized with said motivational content; and
       a wireless transmitter communicably connected with said input receptacle and receiving said exercise programs from said at least one storage medium, said transmitter delivering said exercise programs to said plurality of exercise devices using a wireless carrier signal, wherein said control panel is adapted to enable an exerciser to select one of said plurality of exercise programs at said control panel and activate said control panel such that said wireless transmitter delivers said one of said plurality of exercise programs to said plurality of exercise devices, and wherein said central control unit is adapted to control said plurality of exercise devices in succession without further input from the exerciser at said central control unit or said plurality of exercise devices.

13. The central control unit as recited in claim 12, wherein said support structure comprises a base and a stand extending from said stand.

14. The central control unit as recited in claim 12, wherein said at least one input receptacle comprises at least one of a compact disc player, a videodisc player, a magnetic tape player, a flash memory player, an MP3 player.

15. The central control unit as recited in claim 12, wherein said control panel further comprises at least one input device and at least one output device.

16. The central control unit as recited in claim 15, wherein said at least one input device comprises at least one control that changes at least one operating parameter of the central control unit.

17. The central control unit as recited in claim 15, wherein said at least one output device comprises at least one visual display that depicts a visual representation of said exercise program.

18. The central control unit as recited in claim 15, wherein said at least one output device comprises at least one audio device that broadcasts an audio portion of said plurality of said exercise programs.

19. The central control unit as recited in claim 12, wherein said wireless carrier signal is a signal selected from the group consisting of an infrared signal or a radio signal.

20. The central control unit as recited in claim 12, wherein said control panel further includes one or more controls that can be manipulated to select at least one exercise program from said plurality of exercise programs.

21. The central control unit as recited in claim 12, further comprising at least one receiver, said at least one receiver receiving said exercise program.

22. The central control unit as recited in claim 21, wherein said at least one receiver uses at least one of a USB, Firewire, Ethernet, serial, and SCSI communication protocol to receive said exercise program.

23. The central control unit as recited in claim 21, wherein said at least one receiver receives broadcast signals from a broadcast transmission device.

24. The central control unit as recited in claim 12, wherein said plurality of exercise devices is of a first type of exercise device, said first type of exercise device being selected from the group of aerobic exercise devices or anaerobic exercise devices.

25. The central control unit as recited in claim 12, wherein each of said plurality of exercise devices is either a first type of exercise device or a second type of exercise device, said first type of exercise device and said second type of exercise device being selected from the group of aerobic exercise devices or anaerobic exercise devices.

26. The central control unit as recited in claim 12, wherein each of said plurality of exercise devices is either a first type of exercise device or a second type of exercise device, said first type of exercise device and said second type of exercise device being selected from the group of a treadmill, an elliptical, a weight stack, or a bike.

27. The central control unit as recited in claim 12, wherein, upon selection of said one of said plurality of exercise programs and activation of said control panel, said wireless transmitter delivers said one of said plurality of exercise programs to said plurality of exercise devices without prior communication between the exerciser and said plurality of exercise devices or from said plurality of exercise devices to said central control unit.

28. A central managing unit for managing the operation of a plurality of exercise devices through exercise programming that is selected and activated at the central managing unit by an exerciser and simultaneously delivered to the plurality of exercise devices, the central managing unit comprising:
 a receptacle providing a user interface for the central managing unit; and
 a transmitter supported by the receptacle, the transmitter simultaneously delivering exercise programming to the plurality of exercise devices, the exercise programming comprising control signals synchronized with motivational content for controlling an operation of the plurality of exercise devices and simultaneously providing encouragement and/or instruction to the exerciser, wherein the central managing unit is adapted to:
 enable an exerciser to select and activate exercise programming at the central managing unit, simultaneously deliver the exercise programming to the plurality of exercise devices, control an operation of a first exercise device of the plurality of exercise devices upon selection and activation by the exerciser of exercise programming at the central managing unit and, upon completion of the operation of the first exercise device, automatically control an operation of a second exercise device of the plurality of exercise devices without any additional input from the exerciser at the central managing unit or at the plurality of exercise devices.

29. The central managing unit of claim 28, wherein the receptacle further comprises at least one storage medium, the at least one storage medium storing the exercise programming.

30. The central managing unit of claim 28, wherein the receptacle further comprises an input receptacle that receives at least one storage medium.

31. The central managing unit of claim 28, wherein the central managing unit is adapted to simultaneously deliver the exercise programming to the plurality of exercise devices without prior communication from the plurality of exercise devices to the central managing unit.

32. A central unit configured to transmit motivational content to a plurality of exercise devices, the central unit comprising:
 a receptacle providing a user interface for the central unit; and
 a transmitter supported by the receptacle, the transmitter simultaneously delivering the same exercise programming to the plurality of exercise devices, wherein upon activation of the central unit by a user the exercise programming is adapted to control each of the plurality of exercise devices individually and in succession without additional input from the user prior to the central unit controlling each exercise device of the plurality of exercise devices, wherein the exercise programming includes motivational content.

33. The central unit of claim 32, wherein the exercise programming includes instructional content.

34. The central unit of claim 32, wherein the exercise programming includes control signals for controlling the plurality of the exercise devices.

35. The central unit of claim 32, wherein the delivery of the exercise programming is the initial communication between the central unit and the plurality of exercise devices.

36. The central unit of claim 35, wherein the initial communication is initiated by the user at the central unit.

37. An exercise system comprising:
 a central unit for communicating with a plurality of exercise devices, the central unit comprising:
 a receptacle providing a user interface for the central unit; and
 a transmitter supported by the receptacle, the transmitter delivering exercise programming initiated by an exerciser at the central unit to the plurality of exercise devices, wherein the exercise programming is adapted to control each of the plurality of exercise devices individually and in succession without additional input from the exerciser prior to the central unit controlling each exercise device of the plurality of exercise devices; and wherein each exercise device of the plurality of exercise devices having an input device for receiving the exercise programming.

38. The exercise system of claim 37, wherein the central exercise unit further comprises at least one input port, the input port receiving the exercise programming from a broadcast transmission device.

39. The exercise system of claim 37, wherein the transmitter is a transceiver for:

delivering exercise programming; and receiving feedback signals regarding the performance of exercise at the respective plurality of exercise devices.

40. A central communications unit for communicating with a plurality of exercise devices, the central communications unit comprising:

a receptacle providing a user interface for the central communications unit; and a transmitter supported by the receptacle, the transmitter simultaneously delivering exercise programming to the plurality of exercise devices without prior communication between an exerciser and the plurality of exercise devices or from the plurality of exercise devices to the central communications unit, wherein the exercise programming is adapted to control the plurality of exercise devices individually and in succession without input from the exerciser prior to controlling each exercise device of the plurality of exercise devices.

41. The central communications unit of claim 40, wherein the exercise programming is delivered to the plurality of exercise devices using hardwire connections between the central communications unit and the plurality of exercise devices.

42. The central communications unit of claim 40 further comprising at least one input port, the input port receiving the exercise programming from an Internet address.

43. An exercise system comprising:

a central unit for communicating with a plurality of exercise devices, the central unit comprising:

a receptacle providing a user interface for the central unit; and a transmitter supported by the receptacle, the transmitter delivering exercise programming to the plurality of exercise devices; and wherein each exercise device of the plurality of exercise devices has an input device for receiving the exercise programming, such that an exerciser can (i) initiate exercise programming at the central unit, which is simultaneously sent to a first exercise device and a second exercise device, then (ii) exercise on the first exercise device, and then (iii) exercise on the second exercise device without initiating any communication to the second exercise device or further communication to the central unit prior to exercising on the second exercise device.

* * * * *

UNITED STATES PATENT AND TRADEMARK OFFICE
CERTIFICATE OF CORRECTION

PATENT NO. : 7,537,546 B2  
APPLICATION NO. : 10/674911  
DATED : May 26, 2009  
INVENTOR(S) : Watterson et al.

It is certified that error appears in the above-identified patent and that said Letters Patent is hereby corrected as shown below:

On the Title Page
Item 56, References Cited, Other Publications, Page 3, change "Internet Archive Wayback Machine, archive for www.ifit.com, at http://web.archive,org/web/*/www.ifit.com, Sep. 1, 2003. 1pg" to --Internet Archive Wayback Machine, archive for www.ifit.com, at http://web.archive.org/web/*/www.ifit.com, Sept. 1, 2003. 1pg--
Item 56, References Cited, Other Publications, Page 4, change "Notice of Allowance and Fee(s) Due, date mailed Nov. 24, 2003, 5 pages, U.S. Appl. No. 09/690/701." to --Notice of Allowance and Fee(s) Due, date mailed Nov. 24, 2003, 5 pages, U.S. Appl. No. 09/690,701.--

Drawings
Sheet 7, replace a portion of FIG. 7 with the portion of the figure depicted below, wherein audio/video playback device is labeled 56, speaker is labeled 58, video display is labeled 60, and control signal decoder is labeled 64

Signed and Sealed this  
Eleventh Day of September, 2012

David J. Kappos  
*Director of the United States Patent and Trademark Office*

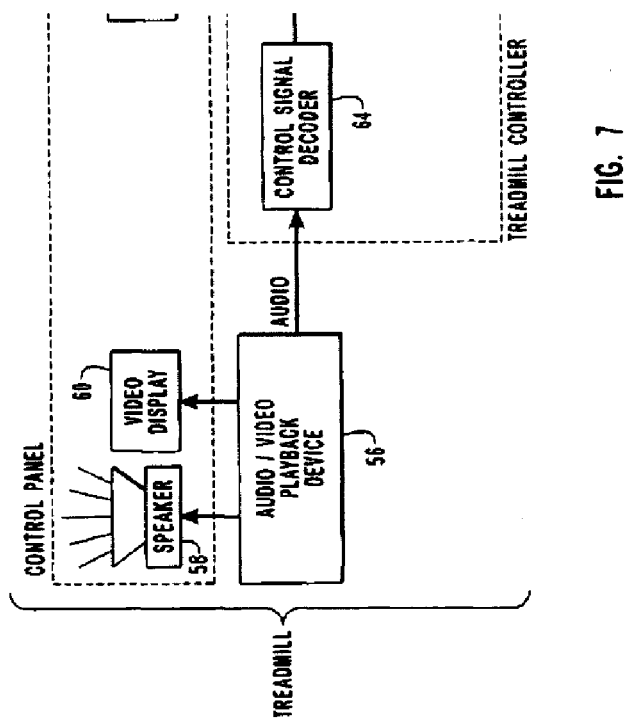

Column 1
Line 56, change "work out" to --workout--

Column 2
Lines 34 and 35, remove [as encouragement is provided to the user]

Column 4
Lines 6 and 7, change "FIG. 10 is a functional block diagram in accordance with an alternative embodiment of the present invention;" to --FIG. 10 is a perspective view of an input receptacle according to one embodiment of the present invention--

Column 7
Line 8, change "The output of the picks up" to --The output that picks up--

Column 8
Line 31, change "treadmills" to --treadmill--

Column 9
Line 47, change "FIGS. 8-13" to --FIGS. 8-12--

Column 11
Line 55, change "can attached" to --can be attached--

Column 12
Line 26, change "motor 40," to --motor 30,--

CERTIFICATE OF CORRECTION (continued)
U.S. Pat. No. 7,537,546 B2

Column 13
Line 50, change "unit 100" to --unit 100,--

Column 15
Line 49, remove [other] after "otherwise"
Line 57, change "module 22" to --module 222--

Column 16
Line 32, insert --may be displayed on display module 218-- after "routines"
Line 48, change "network 230" to --network 230,--
Line 58, change "module 22" to --module 222--

Column 17
Line 13, change "converting" to --converts--
Line 41, change "110a, 10$n$" to --110a-110$n$--

Column 19
Line 26, change "be the imagination" to --by the imagination--